US008518978B2

(12) United States Patent
Hwang et al.

(10) Patent No.: US 8,518,978 B2
(45) Date of Patent: Aug. 27, 2013

(54) PHARMACEUTICAL COMPOSITION FOR PREVENTION AND TREATMENT OF RESTENOSIS COMPRISING ISOXAZOLE DERIVATIVES

(75) Inventors: Sun Gwan Hwang, Daejeon (KR); Sang Rak Choi, Daejeon (KR); Jeong Woo Cho, Daejeon (KR); Sung Jin Bae, Daejeon (KR); Tae Sung Koo, Daejeon (KR); So Young Lee, Daejeon (KR); Kyung Chul Cho, Daejeon (KR); Hyeon Cheol Gwon, Seoul (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 559 days.

(21) Appl. No.: 12/666,785

(22) PCT Filed: Jun. 30, 2008

(86) PCT No.: PCT/KR2008/003821
§ 371 (c)(1),
(2), (4) Date: Sep. 21, 2010

(87) PCT Pub. No.: WO2009/005269
PCT Pub. Date: Jan. 8, 2009

(65) Prior Publication Data
US 2011/0028506 A1 Feb. 3, 2011

(30) Foreign Application Priority Data

Jun. 29, 2007 (KR) .................. 10-2007-0065481
Jun. 30, 2008 (KR) .................. 10-2008-0062297

(51) Int. Cl.
*A61K 31/41* (2006.01)
*A61K 31/34* (2006.01)

(52) U.S. Cl.
USPC .......................... 514/360; 514/461

(58) Field of Classification Search
None
See application file for complete search history.

(56) References Cited

FOREIGN PATENT DOCUMENTS

| WO | WO03013517 | 2/2003 |
| WO | WO2007078113 | 7/2007 |
| WO | WO 2007078113 A1 * | 7/2007 |
| WO | WO 2008070739 A1 * | 6/2008 |
| WO | WO2009005269 A2 | 1/2009 |
| WO | WO2009005269 A3 | 1/2009 |

OTHER PUBLICATIONS

Glagov, Intimal Hyperplasia, Vascular Modeling, and the Restenosis Problem, Circulation, vol. 89, No. 6, Jun. 1994, 2888-2891.*
FDA Clinical Overview for Panel Packet DES Thrombosis Panel, Dec. 7-8, 2006.*
Dussaillant et al., "Small stent size and intimal hyperplasia contribute to restenosis: a volumetric intravascular ultrasound analysis," J. Am. Coll Cardiol, 1995; 26:720-724.
Epstein et al., "The basis of molecular strategies for treating coronary restenosis after angioplasty," J. Am.. Coll Cardiol, 1994; 23:1278-1288.
Hoffmann et al., "Patterns and mechanisms of in-stent restenosis. A serial intravascular ultrasound study," Circulation. Sep. 15, 1996;94(6):1247-54.
Moon et al., "The promise and perils of Wnt signaling through beta-catenin," Science. May 31, 2002;296(5573):1644-6.
Sarembock et al., "Mechanisms of vascular injury from drug-eluting stents," Drug Discovery Today: Disease Mechanisms, vol. 4, Issue 3, Autumn 2007, pp. 141-146.
Ribichini F, et al., Circulation, 1998; 97:147-154, 1998.
Gtagov S, Circulation, 89:2888-2891, 1994.
Palmer RMJ, et al., Nature, vol. 327:524-526, 1987.
Kinsella MG, Wight TN, J. Cell Biol., vol. 102-679-687, 1986.
McNamara CA, et al., J. Clin, Invest., vol.. 91:94-98, 1993.
FDA Clinical Overview for Panel Packet DES Thrombosis Panel Dec. 7-8, 2006.
Finn et al., Circulation 2005; 112-270-278.
Reya T and Clevers H, Nature, 2005, vol. 434: 843-850.
He XC et al., Nat Genetices, 2004, vol. 36:1117-1121.
Tamai K et al., Mol. Cell, 2004, vol. 13; 149-156.
Tamai K et al., Nature, 2000, vol. 407; 530-535.
Reya T et al., Nature, 2003, vol. 423; 409-414.
Trowbridge JJ et al., Nature Med., Dec. 2005; 1-10.
International Search Report and Written Opinion dated Dec. 22, 2008.

* cited by examiner

*Primary Examiner* — Sreeni Padmanabhan
*Assistant Examiner* — Svetlana M Ivanova
(74) *Attorney, Agent, or Firm* — Harness, Dickey & Pierce, P.L.C.; J. Timothy Keane; Kisuk Lee

(57) ABSTRACT

There is provided a pharmaceutical composition for prevention and treatment of restenosis comprising isoxazole derivatives. The pharmaceutical composition includes a therapeutic effective amount of isoxazole derivatives represented by Formula 1 or pharmaceutically available salts thereof. The pharmaceutical composition may be useful to prevent and treat vascular restenosis since the pharmaceutical composition shows an anti-restenosis activity and accelerates the re-endothelization.

19 Claims, 15 Drawing Sheets

CONTROL
(75% DMF)

ISOXAZOLE
(20 ug/kg/day)

OCCURRENCE OF
RE-ENDOTHELIZATION
ON DAMAGED CAROTID
ARTERY SURFACE

EC STAINING USING ANTI-VWF(VON WILLEBRAND FACTOR)

PHARMACEUTICAL COMPOSITION FOR PREVENTION AND TREATMENT OF RESTENOSIS COMPRISING ISOXAZOLE DERIVATIVES

TECHNICAL FIELD

The present invention relates to a pharmaceutical composition for prevention and treatment of restenosis, and more particularly, to a pharmaceutical composition for prevention and treatment of restenosis comprising isoxazole derivatives or their pharmaceutically available salts as effective components.

BACKGROUND ART

As one of the methods for treating ischemic diseases represented by angina pectoris or myocardial infarction, percutaneous transluminal coronary angioplasty (PTCA) has recently been widely used instead of bypass surgery. In this case, the PTCA is performed by transcutaneously inserting a special catheter having a balloon attached to a front end thereof into a stenotic site of the coronary artery from the peripheral artery and expanding the stenotic site by inflating the balloon. The coronary angioplasty using the balloon catheter has been evaluated as an excellent therapeutics since it has a relatively high improvement rate of angina pectoris and a low risk to induce the onset of myocardial infarction. However, the restenosis in the same site develops at a frequency of 40 to 50% after the coronary angioplasty using the balloon catheter. In this case, the PTCA or the bypass surgery should be performed again.

In order to solve the above problems, a method using a stent has been used to treat a stenosed blood vessel and maintain a normal blood flow by inserting a stainless steel metal stent into a stenosed blood vessel and inflating the stenosed blood vessel into an original size of blood vessel. It was reported that this coronary stenting lowers a restenosis rate by approximately 10%. However, the method using a stent also has problems that the restenosis relapses at a high frequency, and it is also difficult to apply a stent to a bent blood vessel since the stent lack the flexibility.

The mechanism for the occurrence of in-stent restenosis was studied to solve the above problems. As a result, it was reported that, unlike the mechanism in the intervention using a balloon, the mechanism of restenosis after stenting operation is due to the hyperplasia of neointima caused by the barotraumas of vessel wall and the continuous stimulus by foreign bodies, and the pseudo in-stent restenosis may occur when the blood vessel is not sufficiently inflated during the stenting operation (see Hoffman R, et al., Circulation, 94:1247-1254, 1966: Dussainllant G R, et al., J. Am. Coll. Cardiol., 26:720-724, 1995). Recently, it has been known that the hyperplasia reaction to the damage of endothelial cells is associated with the polymorphism of an angiotensin converting enzyme (ACE) gene. In the case, a D/D genetic trait was observed in 80% of diffuse in-stent restenotic lesions, and found in 36% of focal lesions, which indicates that the genetic trait is one of factors that can affect the restenosis (see Ribichini F, et al., Circulation, 97:141-154, 1998). Also, it was expected that the neointimal formation caused by the proliferation of vascular smooth muscle cells in media of blood vessel and the migration of the vascular smooth muscle cells into the lining membrane plays the most important role in the restenosis mechanism. From these research results, it has recently been considered that the blood vessel restenosis occurs due to the proliferation of vascular smooth muscle cells in damaged blood vessel after the intervention, the neointimal hyperplasia caused by growth factors and cytoplasmic matrix, the vascular remodeling by the reaction of vessel wall to the dynamic changes in blood vessel, etc. (see Epstein S E., et al., J. Am. Coll. Cardiol., 23:1278-1288, 1994; Glagov S, Circulation, 89:28888-28891, 1994).

Normal vascular smooth muscle cell does not grow, but the division, migration and proliferation of the vascular smooth muscle cell are induced through the signal transduction cascades when media of endothelial cell is damaged by a stenting operation, etc. The proliferation mechanisms of vascular smooth muscle cell include the removal of proliferation-inhibiting factors, the activation of proliferation-promoting factors by the damage of normal endothelial cell, the transduction of proliferation-promoting signals through receptors on a cell surface of vascular smooth muscle cell, and the changes in cell cycle by the proliferation-promoting signals transduced into the nucleus of the vascular smooth muscle cell, etc. The normal endothelial cell secretes factors that inhibit the proliferation of vascular smooth muscle cell, but it has been reported that, when the endothelial cell is damaged, the secretion of these factors is inhibited, and the proliferation of the vascular smooth muscle cell is induced by thrombin, a fibroblast growth factor (FGF) and a platelet-derived growth factor (PDGF) that are secreted from activated platelet, and oxygen free radicals generated by the cell damage (see Palmer R M J, et al., Nature, 327:524-526. 1987; Kinsella M G, Wight T N, J. Cell Biol., 102:678-682, 1986: McNamara C A, et al., J. Clin. Invest., 91:94-98, 1993).

New PTCA equipments such as laser angioplasty, high-speed rotational atherectomy and coronary angioplasty using a cutting balloon have been introduced to prevent the restenosis, and there have also been attempts to prevent the restenosis after the coronary angioplasty by using drugs such as an anti-platelet agent, an antithrombotic agent, a vasodilator, a cytostatic agent, etc. Among them, a drug-eluting stent whose surface is coated with a cytostatic agent such as rapamycin or paclitaxel has been proven to be the most effective. These drugs potently inhibit the division, migration and proliferation of vascular smooth muscle cells in blood vessel, which are the cause of restenosis. Two kinds of drug-eluting stents had been recognized to have such excellent effect to inhibit the restenosis that the drug-eluting stents take over 90% of the US coronary angioplasty market within two years after the drug-eluting stents was launched 2004 by US.

However, it was reported that the drug-eluting stent using a cytostatic agent has a risk to increase the occurrence of late stent thrombosis in patents after one or more months of the stenting operation (2006 World Cardiology Congress in Barcelona). Accordingly, the FDA recommended that patients take an antithrombotic agent for at least one year after the stenting operation, and be traced to check the risk of late stent thrombosis (see http://www.fda.govarms/dockets/ac/06/briefing/2006-4253b1_01.pdf). There may be various causes of these side effects of the drug-eluting stents, but one of the most important causes is that wounds of vessel wall in a stented site during the stenting procedure are not healed or their healing is delayed (see Renu Virmani, Circulation 2005; 112; 270-278). The drugs themselves are considered as the cause of the delay of wound healing in the vessel wall. All of the recently used drugs are cytostatic agents, and these cytostatic agents inhibit the division, migration and proliferation of vascular endothelial cell that serve to heal wounds of the vessel wall, as well as inhibit the division, migration and proliferation of vascular smooth muscle cell that are the causes of restenosis. That is, these drugs do not have selectivity toward smooth muscle cell, so that they have an effect to inhibit the restenosis and also a side effect to delay the wound healing of the vessel wall since the drugs do not have certain selectiveness against cells (Sarembock, Drug Discov Today: Dis Mech (2007), doi:10.1016/j.ddmec.2007.10.007). Therefore, there is an urgent demand for development of medical supplies that prevent the restenosis and also has no side effect to inhibit the wound healing of the vessel wall.

Meanwhile, it has been known that "Wnt" protein is a secretory glycoprotein that has a molecular weight of approximately 40 kDa and is rich in cystein, and is associated with various developmental processes including cell proliferation and differentiation and cell polarity (Moon R T et al., *Science,* 2002; Reya T and Clevers H, *Nature,* 2005). It has been reported that 19 Wnt proteins are identified in human, and 10 frizzled proteins and 2 co-receptor (LRP5 and 6) that function as a Wnt receptor are also present in human (He X C et al., *Nat Genet,* 2004; Tamai K et al, *Mol Cell,* 2004; Tamai K et al., *Nature,* 2000).

Recently, it was reported that the Wnt signal transduction pathway plays an important role in the maintenance and differentiation and growth promotion of stem cell (Reya T et al., Nature., 2003; Trowbridge J J et al., Nature Med., 2006), and therefore there are many attempts to develop the Wnt proteins as substances for re-generation of tissues, prevention of hair loss, haematopoiesis, and promotion of growth, maintenance and differentiation of stem cell.

The present inventors have ardent attempts to solve the above problems, and found that isoxazole derivatives and pharmaceutically available salts thereof that serve as agonists having an effect to agonize the Wnt/β-catenin signal transduction is effective to prevent and treat restenosis. Therefore, the present invention was completed on the basis of the above facts.

DISCLOSURE OF INVENTION

Technical Problem

The present invention is designed to solve the problems of the prior art, and therefore it is an object of the present invention to provide a pharmaceutical composition having an effect to prevent and treat restenosis since the pharmaceutical composition comprises isoxazole derivatives or their pharmaceutically available salts as effective components.

Also, it is another object of the present invention to provide a method for prevention or treatment of vascular restenosis without any of side effects of late stent thrombosis caused by the wound healing inhibition in vascular endothelial cell by employing the isoxazoles derivatives or their pharmaceutically available salts as an effective component to give the anti-restenosis activity and accelerate the re-endothelization.

Technical Solution

Prior to the detailed description of this specification of the present invention, sane terms used in this application are defined, as follows.

a) Alkyl group: refers to a linear or branched, saturated or unsaturated hydrocarbon containing 1 to 10 carbon atoms, wherein one or more hydrogen may be substituted with one or more substituent selected from a group consisting of acyl, amino, carboalkoxy, carboxy, carboxyamino, —O-carbamoyl (—O—(C=O)—NH$_2$), cyano, halo, hydroxy, nitro, thio, alkyl, cycloalkyl, aryl, alkoxy, aryloxy, sulfoxy and guanido to the maximum possible number, irrespective of the order and kind thereof.

b) Cycloalkyl group: refers to a non-aromatic, monocyclic or polycyclic ring hydrocarbon compound, whether saturated or partially unsaturated, which consists of 3-12 ring constitutional members with 0~5 hetero atoms, such as oxygen, sulfur, nitrogen, etc., therein. It may 3-12-gon single ring compound or fused ring compound, wherein one or more hydrogen may be substituted with one or more substituent selected from a group consisting of acyl, amino, carboalkoxy, carboxy, carboxyamino, —O-carbamoyl (—O—(C=O)—NH$_2$), cyano, halo, hydroxy, nitro, thio, alkyl, cycloalkyl, aryl, alkoxy, aryloxy, sulfoxy, guanido to the maximum possible number, irrespective of the kind and order thereof.

Concrete examples of the cycloalkyl group include, but are not limited to, cyclopropyl, cyclobutyl, cyclopentyl, cyclohexyl, cycloheptyl, cyclooctyl, morpholinyl, homomorpholinyl, thiomorpholinyl, homothiomorpholinyl, thiomorpholinyl S-oxide, thiomorpholinyl S,S-dioxide, piperidinyl, homopiperidinyl, piperazinyl, homopiperazinyl, pyrrolidinyl, pyrrolinyl, tetrahydropyranyl, tetrahydrofuranyl, tetrahydrothienyl, oxazolidinonyl, dihydropyrazolyl, dihydropyrrolyl, dihydropyrazinyl, dihydropyridinyl, dihydropyrimidinyl, dihydrofuryl, and dihydropyranyl.

c) Aryl group: refers to aromatic group including an aromatic single or fused ring hydrocarbon consisting of 5 to 15 ring members and heteroaromatic group with 1 to 5 heteroatoms, such as oxygen, sulfur or nitrogen, wherein one or more hydrogen may be substituted with one or more substituent selected from a group consisting of acyl, amino, carboalkoxy, carboxy, carboxyamino, —O-carbamoyl (—O—(C=O)—NH$_2$), cyano, halo, hydroxy, nitro, thio, alkyl, cycloalkyl, aryl, alkoxy, aryloxy, sulfoxy, guanido, and combinations thereof to the maximum possible number, irrespective of the order and kind thereof.

Concrete example of the aryl group include, but are not limited to, phenyl, 1-naphtyl, 2-naphtyl, pyridinyl, pyrimidinyl, quinolinyl, benzothienyl, indolyl, pyrazinyl, isoindolyl, isoquinolyl, qunazolinyl, quinoxalinyl, phthalazinyl, imidazolinyl, isoxazolyl, pyrazolyl, oxazolyl, thiazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, cinnolinyl, carbazolyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiopyranyl, benzopyranyl, benzothiopyranyl, coumarinyl, isocoumarinyl, chromonyl, chromanonyl, pyridinyl-N-oxide, tetrahydroquinolinyl-N-oxide, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyrazinyl-N-oxide, quinolinyl-N-oxide, indolyl-N-oxide, indolinyl-N-oxide, pyrazinyl-N-oxide, isoquinolyl-N-oxide, qunazolinyl-N-oxide, quinoxalinyl-N-oxide, phthalazinyl-N-oxide, imidazolinyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, and tetrazolyl-N-oxide.

d) Halo: generally refers to fluoro, chloro, bromo and iodo.

For convenience of explanation, the terms used in the present invention will be used in the abbreviated forms defined below.

N,N-dimethylformamide: DMF
tetrahydrofuran: THF
1-(3-dimethylaminopropyl)-3-ethylcarbodiimide: EDC
1-hydroxybenzotriazole hydrate: HOBt
1,1'-carbonyldiimidazole: CDI
diphenylphosphoryl azide: DPPA
triethylamine: TEA
methyl: Me
ethyl: Et Hereinafter, exemplary embodiments of the present invention will be described in more detail.

According to an aspect of the present invention, there is provided a pharmaceutical composition for prevention and treatment of restenosis comprising a therapeutic effective amount of isoxazole derivatives represented by the following Formula 1 or pharmaceutically available salts thereof:

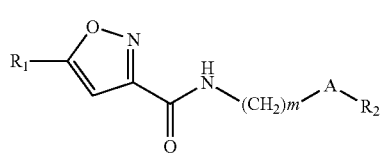

[Formula 1]

wherein, $R_1$ is phenyl, furanyl or thienyl that is substituted or un-substituted with at least one substituent selected from the group consisting of acyl, amino, carboalkoxy, carboxy, carboxyamino, —O-carbamoyl (—O—(C=O)—NH$_2$), cyano, halo, hydroxy, nitro, thio, alkyl, cycloalkyl, aryl, alkoxy, aryloxy, sulfoxy and guanido, m is 2 or 3, A is a bond, O, S, SO, or S(=O)$_2$, and $R_2$ is imidazolyl, pyrazolyl, triazolyl, tetrazolyl or pyridinyl that is substituted or unsubstituted with at least one substituent selected from the group consisting of acyl, amino, carboalkoxy, carboxy, carboxyamino, —O-carbamoyl (—O—(C=O)—NH$_2$), cyano, halo, hydroxy, nitro, thio, alkyl, cycloalkyl, aryl, alkoxy, aryloxy, sulfoxy and guanido.

In addition to the compounds represented by Chemical Formula 1, pharmaceutically acceptable acid or base addition salts and stereochemical isomers thereof are in the range of the isoxazole derivatives of the present invention. As long as it maintains the activity of the parent compound in the subjects administered therewith without underisable effects, any salt is within the scope of the present invention, and no particular limitation is imposed thereon. The salts may be inorganic or organic salts. Preferable are salts of acetic, nitric, aspartic, sulfonic, sulfuric, maleic, glutamic, formic, succinic, phosphoric, phthalic, tannic, tartaric, hydrobromic, propionic, benzenesulfonic, benzoic, stearic, esyl, lactic, bicarbonic, bisulfuric, bitartaric, oxalic, butyric, calcium edetate, camsylic, carbonic, chlorobenzoic, citric, edetic, toluenesulfonic, edisylic, esylic, fumaric, gluceptic, panic, gluconic, glycollylarsanilic, methylnitric, polygalactouronic, hexylresorcinoic, malonic, hydrabamic, hydrochloric, hydroiodic, hydroxynaphthoic, isethionic, lactobionic, mandelic, estolic, methylsulfuric, mucic, napsylic, muconic, p-nitromethanesulfonic, hexamic, pantothenic, monohyrogen phosphoric, dihyrogen phosphoric, salicylic, sulfamic, sulfanilic, methanesulfonic, or teoclic acid.

Also, the form of basic salt may include, for example, ammonium salt, alkali metal salts and alkaline earth metal salts such as lithium sodium potassium, magnesium and calcium salts, organic base salts, such as bezathine, N-methyl-D-glucamine, hydrabamine salts, and amino acids such as arginine and lysine.

Meanwhile, the form of salt may be converted to free forms by treatment with suitable bases or acids.

The term 'addition salt' as used herein means salts that include solvates which compounds of Chemical Formula 1 or salts thereof can form. The solvates may be exemplified by hydrates and alcoholates.

As used herein, the term 'stereochemical isomers of compounds of Chemical Formula 1' refers to all possible forms that the compounds of Chemical Formula 1 can have. Unless specified or mentioned otherwise, the chemical names of the compounds of Chemical Formula 1 indicate mixtures of all possible stereochemical isomers, including all diastereomers and enantiomers of basic molecular structures.

Particularly, each chiral center may have either R or S-configuration, and substitutents on bivalent cyclic (partially) saturated radicals may have a cis- or trans-configuration. Compounds having double bonds may have E- or Z-stereochemistry, if present. All stereochemical isomers of the compounds represented by Chemical Formula 1 are intended to be included within the scope of the present invention.

Among the isoxazole derivatives according to one exemplary embodiment of the present invention, more preferred examples of the isoxazole derivatives includes, but are not particularly limited to, the following derivatives (1) to (70).

Derivative 1: 5-furan-2-yl-isoxazole-3-carboxylic acid (3-imidazol-1-yl-propyl)-amide Derivative 2: 5-furan-2-yl-isoxazole-3-carboxylic acid (2-pyridin-2-yl-ethyl)-amide Derivative 3: 5-furan-2-yl-isoxazole-3-carboxylic acid (2-pyridin-3-yl-ethyl)-amide Derivative 4: 5-furan-2-yl-isoxazole-3-carboxylic acid (2-imidazol-1-yl-ethyl)-amide Derivative 5 5-furan-2-yl-isoxazole-3-carboxylic acid (2-pyridin-4-yl-ethyl)-amide Derivative 6: 5-furan-2-yl-isoxazole-3-carboxylic acid [2-(2-methyl-imidazol-1-yl)-ethyl]-amide Derivative 7: 5-furan-2-yl-isoxazole-3-carboxylic acid [2-(5-methyl-imidazol-1-yl)-ethyl]-amide Derivative 8: 5-furan-2-yl-isoxazole-3-carboxylic acid [2-(4-methyl-imidazol-1-yl)-ethyl]-amide Derivative 9: 5-furan-2-yl-isoxazole-3-carboxylic acid (2-[1,2,4]triazol-1-yl-ethyl)-amide Derivative 10: 5-furan-2-yl-isoxazole-3-carboxylic acid (2-pyrazol-1-yl-ethyl)-amide Derivative 11: 5-furan-2-yl-isoxazole-3-carboxylic acid (2-[1,2,3]triazol-1-yl-ethyl)-amide Derivative 12: 5-furan-2-yl-isoxazole-3-carboxylic acid (2-[1,2,3]triazol-2-yl-ethyl)-amide Derivative 13: 5-furan-2-yl-isoxazole-3-carboxylic acid (2-tetrazol-2-yl-ethyl)-amide Derivative 14: 5-furan-2-yl-isoxazole-3-carboxylic acid (2-tetrazol-1-yl-ethyl)-amide Derivative 15: 5-furan-2-yl-isoxazole-3-carboxylic acid [3-(2-methyl-imidazol-1-yl)-propyl]-amide Derivative 16: 5-furan-2-yl-isoxazole-3-carboxylic acid (3-pyrazol-1-yl-propyl)-amide Derivative 17: 5-furan-2-yl-isoxazole-3-carboxylic acid (3-[1,2,3]triazol-1-yl-propyl)-amide Derivative 18: 5-furan-2-yl-isoxazole-3-carboxylic acid (3-[1,2,3]triazol-2-yl-propyl)-amide Derivative 19: 5-furan-2-yl-isoxazole-3-carboxylic acid (3-[1,2,4]triazol-1-yl-propyl)-amide Derivative 20: 5-furan-2-yl-isoxazole-3-carboxylic acid (3-tetrazol-1-yl-propyl)-amide Derivative 21: 5-furan-2-yl-isoxazole-3-carboxylic acid (3-tetrazol-2-yl-propyl)-amide
Derivative 22: 5-furan-2-yl-isoxazole-3-carboxylic acid [3-(4-methyl-imidazol-1-yl)-propyl]-amide
Derivative 23: 5-phenyl-isoxazole-3-carboxylic acid (3-imidazol-1-yl-propyl)-amide
Derivative 24: 5-phenyl-isoxazole-3-carboxylic acid (2-imidazol-1-yl-ethyl)-amide
Derivative 25: 5-o-tolyl-isoxazole-3-carboxylic acid (3-imidazol-1-yl-propyl)-amide
Derivative 26: 5-m-tolyl-isoxazole-3-carboxylic acid (3-imidazol-1-yl-propyl)-amide
Derivative 27: 5-p-tolyl-isoxazole-3-carboxylic acid (3-imidazol-1-yl-propyl)-amide
Derivative 28: 5-(2-fluoro-phenyl)-isoxazole-3-carboxylic acid (3-imidazol-1-yl-propyl)-amide
Derivative 29: 5-(3-fluoro-phenyl)-isoxazole-3-carboxylic acid (3-imidazol-1-yl-propyl)-amide
Derivative 30: 5-(4-fluoro-phenyl)-isoxazole-3-carboxylic acid (3-imidazol-1-yl-propyl)-amide
Derivative 31: 5-(4-fluoro-phenyl)-isoxazole-3-carboxylic acid (3-[1,2,4]triazol-1-yl-propyl)-amide
Derivative 32: 5-(2-fluoro-phenyl)-isoxazole-3-carboxylic acid (2-imidazol-1-yl-ethyl)-amide
Derivative 33: 5-(4-fluoro-phenyl)-isoxazole-3-carboxylic acid (2-imidazol-1-yl-ethyl)-amide
Derivative 34: 5-(4-fluoro-phenyl)-isoxazole-3-carboxylic acid (2-pyrazol-1-yl-ethyl)-amide
Derivative 35: 5-(4-fluoro-phenyl)-isoxazole-3-carboxylic acid (2-[1,2,4]triazol-1-yl-ethyl)-amide
Derivative 36: 5-(4-fluoro-phenyl)-isoxazole-3-carboxylic acid (2-[1,2,3]triazol-2-yl-ethyl)-amide
Derivative 37: 5-(4-fluoro-phenyl)-isoxazole-3-carboxylic acid (2-[1,2,3]triazol-1-yl-ethyl)-amide
Derivative 38: 5-(4-fluoro-phenyl)-isoxazole-3-carboxylic acid (2-tetrazol-2-yl-ethyl)-amide
Derivative 39: 5-(4-chloro-phenyl)-isoxazole-3-carboxylic acid (3-[1,2,4]triazol-1-yl-propyl)-amide
Derivative 40: 5-(4-chloro-phenyl)-isoxazole-3-carboxylic acid (2-[1,2,4]triazol-1-yl-ethyl)-amide
Derivative 41: 5-(4-chloro-phenyl)-isoxazole-3-carboxylic acid (3-imidazol-1-yl-propyl)-amide
Derivative 42: 5-(2-methoxy-phenyl)-isoxazole-3-carboxylic acid (3-imidazol-1-yl-propyl)-amide
Derivative 43: 5-(3-methoxy-phenyl)-isoxazole-3-carboxylic acid (3-imidazol-1-yl-propyl)-amide
Derivative 44: 5-(4-methoxy-phenyl)-isoxazole-3-carboxylic acid (3-imidazol-1-yl-propyl)-amide
Derivative 45: 5-(3-nitro-phenyl)-isoxazole-3-carboxylic acid (3-imidazol-1-yl-propyl)-amide
Derivative 46: 5-(4-nitro-phenyl)-isoxazole-3-carboxylic acid (3-imidazol-1-yl-propyl)-amide
Derivative 47: 5-(3-amino-phenyl)-isoxazole-3-carboxylic acid (3-imidazol-1-yl-propyl)-amide
Derivative 48: 5-(4-amino-phenyl)-isoxazole-3-carboxylic acid (3-imidazol-1-yl-propyl)-amide
Derivative 49: 5-thiophen-2-yl-isoxazole-3-carboxylic acid (3-imidazol-1-yl-propyl)-amide
Derivative 50: 5-thiophen-2-yl-isoxazole-3-carboxylic acid (3-[1,2,4]-triazol-1-yl-propyl)-amide
Derivative 51: 5-thiophen-2-yl-isoxazole-3-carboxylic acid (2-imidazol-1-yl-ethyl)-amide
Derivative 52: 5-thiophen-2-yl-isoxazole-3-carboxylic acid (2-pyrazol-1-yl-ethyl)-amide
Derivative 53: 5-thiophen-2-yl-isoxazole-3-carboxylic acid (2-[1,2,4]triazol-1-yl-ethyl)-amide
Derivative 54: 5-thiophen-2-yl-isoxazole-3-carboxylic acid (2-[1,2,3]triazol-1-yl-ethyl)-amide
Derivative 55: 5-thiophen-2-yl-isoxazole-3-carboxylic acid (2-[1,2,3]triazol-2-yl-ethyl)-amide
Derivative 56: 5-thiophen-2-yl-isoxazole-3-carboxylic acid (2-pyridin-3-yl-ethyl)-amide
Derivative 57: 5-thiophen-2-yl-isoxazole-3-carboxylic acid (2-pyridin-4-yl-ethyl)-amide
Derivative 58: 5-(5-bromo-thiophen-2-yl)-isoxazole-3-carboxylic acid (3-imidazol-1-yl-propyl)-amide
Derivative 59: 5-furan-3-yl-isoxazole-3-carboxylic acid (3-imidazol-1-yl-propyl)-amide
Derivative 60: 5-furan-3-yl-isoxazole-3-carboxylic acid (3-[1,2,4]-triazol-1-yl-propyl)-amide
Derivative 61: 5-furan-3-yl-isoxazole-3-carboxylic acid (2-[1,2,4]-triazol-1-yl-ethyl)-amide
Derivative 62: 5-thiophen-3-yl-isoxazole-3-carboxylic acid (3-[1,2,4]-triazol-1-yl-propyl)-amide
Derivative 63: 5-thiophen-3-yl-isoxazole-3-carboxylic acid (3-imidazol-1-yl-propyl)-amide
Derivative 64: 5-thiophen-3-yl-isoxazole-3-carboxylic acid (2-imidazol-1-yl-ethyl)-amide
Derivative 65: 5-thiophen-3-yl-isoxazole-3-carboxylic acid (2-[1,2,4]-triazol-1-yl-ethyl)-amide
Derivative 66: 5-furan-2-yl-isoxazole-3-carboxylic acid [2-(pyridin-2-yl-oxy)-ethyl]-amide
Derivative 67: 5-thiophen-2-yl-isoxazole-3-carboxylic acid [2-(pyridin-2-yl-oxy)-ethyl]-amide
Derivative 68: 5-thiophen-2-yl-isoxazole-3-carboxylic acid [2-(1-methyl-1H-tetrazol-5-yl-sulfanyl)-ethyl]-amide
Derivative 69: 5-thiophen-2-yl-isoxazole-3-carboxylic acid [3-(4H-[1,2,4]triazol-3-yl-sulfanyl)-propyl]-amide
Derivative 70: 5-furan-2-yl-isoxazole-3-carboxylic acid [2-(4-methyl-4H-[1,2,4]triazol-3-yl-sulfonyl)-ethyl]-amide According to another aspect of the present invention, there is also provided a method for prevention or treatment of vascular restenosis without any of side effects of late stent thrombosis by employing the isoxazoles derivatives represented by the Formula 1 or their pharmaceutically available salts as an effective component to give the anti-restenosis activity and accelerate the re-endothelization.

The vascular restenosis may includes, but is not particularly limited to, coronary restenosis after percutaneous transluminal coronary angioplasty (PTCA), restenosis after percutaneous intervention for cerebral and peripheral vascular diseases, vascular stenosis after various vascular surgeries, vascular stenosis after bypass operation and arteriovenous fistula angioplasty, stenosis after self-blood vessel and artificial blood vessel transplantation, and arteriosclerosis.

The isoxazole derivatives of the Formula 1 according to one exemplary embodiment of the present invention may be prepared from known compounds, or compounds that may be easily prepared from the known compounds by any person having ordinary skills regarding the field of compound synthesis in the art to which the present invention pertains. Therefore, the description of a preparation method of isoxazole derivatives proposed herein is just a preferable example for the purpose of illustrations only and the order of unit operations may be selectively changed, if necessary, not intended to limit the scope of the invention.

First of all, the method for preparation of isoxazole derivatives of Formula 1 will be described in detail with reference to the following Scheme 1.

[Scheme 1]

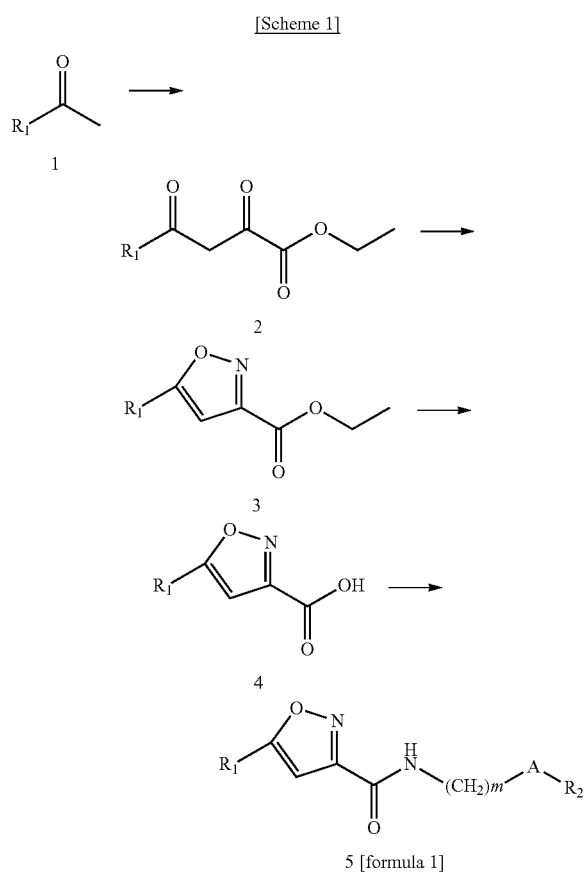

5 [formula 1]

The commercially available starting material (1) may be treated, preferably with 1.0 M sodium ethoxide, in an absolute ethanol solution, and reacted with diethyl oxalate to obtain an intermediate (2). Next, the intermediate (2) may be treated with hydroxylamine in an absolute ethanol solution to obtain an isoxazole intermediate (3). Then, the intermediate (3) may be treated, preferably with a 1N lithium hydroxide aqueous solution, at the presence of THF and methanol solvents to synthesize a carboxylic acid intermediate (4). The intermediate (4) may react with desired amine to obtain the final isoxazole compound (5) (a compound represented by the Formula 1).

Also, the compound of the Formula 1 according to one exemplary embodiment of the present invention has an effect to agonize the Wnt/β-catenin signal transduction, as seen from the results of later-described Examples. Therefore, the present invention provides a composition having an effect to agonize the Wnt/β-catenin signal transduction, essentially comprising a therapeutic effective amount of the isoxazole derivatives represented by the Formula 1, or pharmaceutically available salts and pharmaceutically available carriers thereof.

In the preparation of the pharmaceutical composition, the carriers may be selected according to the formulations to be prepared, and the formulations may be prepared by mixing the carrier with the active components, isoxazole derivatives of the Formula 1, at a suitable mixing ratio.

That is to say, the active components may be formulated into an oral, parenteral, injectable or transcutaneous formulation according to the desired uses, and are prepared in a unit dosage form in the aspect of the easy administration and the dose uniformity.

The administration of the pharmaceutical composition according to one exemplary embodiment of the present invention may comprise intraperitoneal, intramuscular and subcutaneous administrations, as well as the oral administration, but the parenteral administration is preferred. For example, a pharmaceutical composition may be administered with controlled release by inserting an osmotic pump into human, and be also topically administered parenterally into a stent in the form of a coating agent. Also, it is preferred to topically administer the pharmaceutical composition according to one exemplary embodiment of the present invention in the form of a coating agent, alone or in combination of the conventional other drugs. In this case, a coating method follows a conventional method of coating the stent with a drug. As the coating method, a method may be used, for example including: mixing a drug with various polymers used for coating the stent, coating a stent with a drug mixture using a coating method such as drop and spin and sterilizing the coated stent.

Most preferably, the pharmaceutical composition according to one exemplary embodiment of the present invention may be topically administered parenterally in the form of a stent coating agent.

Conventional pharmaceutical carriers may be used for the preparation of oral formulations. For example, water, glycol, oil, alcohol and the like may be used as the carrier in the case of the oral liquid formulations such as suspensions, syrups, elixirs and solutions, and starch, sugar, kaolin, lubricants, binders, disintegrants and the like may be used as the carrier in the case of the solid formulations such as powders, pills, capsules and tablets. The tablets and the capsules are in the most convenient form of dosage in consideration of the easy administration, and it is more preferred to prepare tablets and pills in the form of an enteric formulation.

In the case of the parenteral formulations, sterile water is generally used as the carrier. In this case, the parenteral formulations may further comprise other components such as a solubilizer.

The injectable formulation, for example a sterile injectable aqueous or oily suspension, may be prepared with a suitable dispersing, wetting or suspending agent according to the known methods. Solvent that may be used herein include water, Ringer's solution and isotonic NaCl solution, and a sterile fixed oil is also generally used as the solvent or suspended medium. Any of the non-pungent fixed oils containing mono- or di-glyceride may be used for this purpose, and other fatty acids such as oleic acid may be used for the injectable formulation.

In the case of the transcutaneous formulation, infiltration promoters and/or suitable wetting agents as the carrier may be optionally used together with suitable additives that do not have any irritation to skin. There is no particular limitation on the additives when the additives are of help to promote their administration through the skin or prepare a desired composition. Also, the transcutaneous formulation may be administered in various forms such as transcutaneous patches, creams or ointments.

Meanwhile, in order to prevent the active components according to the present invention from being swiftly removed from human bodies, the composition comprising the isoxazole derivatives according to one exemplary embodiment of the present invention may be formulated into a sustained-released formulation. In this case, specific examples of carriers that may be used herein include implants, miroencapsulated delivery systems, biodegradable/biocompatible polymers, etc. that are known in the art.

The expression 'therapeutically effective amount' means an amount of an active component that is effective to relieve or reduce symptoms of diseases in need of treatment, or reduce or delay the onset of clinical markers or symptoms of diseases in need of prevention. The therapeutically effective amount may be determined from experiences by performing experiments on corresponding compounds in the known in vivo and ex vivo model systems for diseases in deed of treatment.

When the active components, particularly the isoxazole derivatives of Formula 1, in the composition according to one exemplary embodiment of the present invention are administered for the clinical purpose, a daily dosage where the active components may be administered to hosts in single or divided doses is more preferably in a range of from 0.1 to 100 mg per 1 kg of body weight, but the dose equivalent to certain patients may be varied with certain compounds to be used, weight, gender and health status of patients, diet, time of administration of drugs, routes of administration, excretion rate, mixture of drugs, severity of diseases, etc.

The isoxazole derivatives of Formula 1 may be used to formulate an effective pharmaceutical composition into their prodrug forms, etc., when necessary.

Also, the composition according to one exemplary embodiment of the present invention may further comprise other components that do not inhibit, or supplement the action of the active components, and may be formulated into other various forms known in the art. The composition according to one exemplary embodiment of the present invention may preferably further comprise a blood vessel restenosis inhibitor such as rapamycin or paclitaxel known in the prior art.

Advantageous Effects

As described above, the pharmaceutical composition according to one exemplary embodiment of the present invention may be useful to prevent late stent thrombosis that is one of the side effects of the conventional drug-eluting stents since the pharmaceutical composition shows an anti-restenosis activity and accelerates the re-endothelization.

BEST MODE FOR CARRYING OUT THE INVENTION

Figure 1:
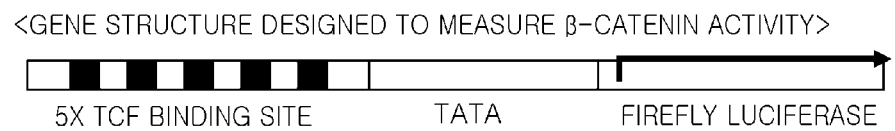
FIG. 1 is a diagram illustrating a gene structure designed to determine an effect of isoxazole derivative on β-catenin activity.

Hereinafter, exemplary embodiments of the present invention will be described in more detail. However, it is understood that the description proposed herein is just a preferable example for the purpose of illustrations only, not intended to limit the scope of the invention.

Preparative Example 1

Preparation of 5-furan-2-yl-isoxazole-3-carboxylic acid (3-imidazol-1-yl-propyl)-amide 5-Furan-2-yl-isoxazole-3-carboxylic acid (3-imidazol-1-yl-propyl)-amide (derivative 1) was prepared through the pathway represented by the following Scheme 2. Each step of the reaction pathway is described in more detail, as follows.

[Scheme 2]

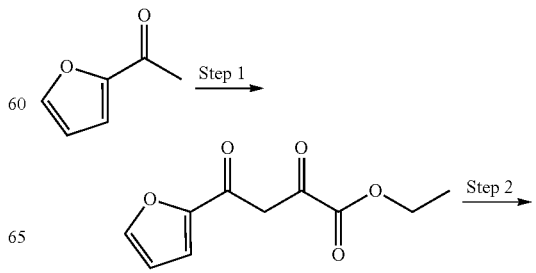

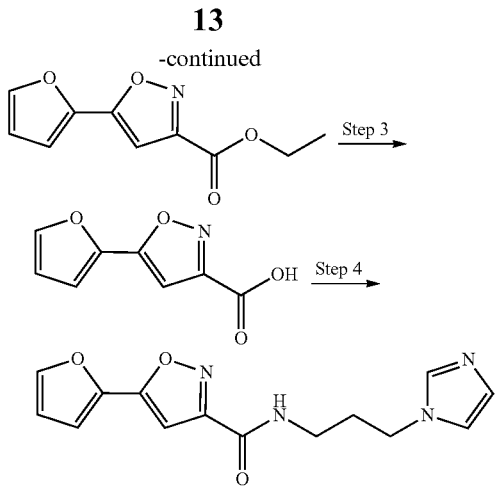

1) Step 1: Preparation of 4-furan-2-yl-2,4-dioxo-butyric acid ethyl ester

To a solution of sodium ethoxide (6.81 g) in absolute ethanol (200 mL). was slowly added 2-acetylfuran (5.01 mL) at 0° C. The resulting solution was stirred at 0° C. for 2 hours, and diethyl oxalate (9.30 mL) was slowly added to the solution. The resulting solution was stirred for 18 hours, and the reaction was quenched with 1N hydrochloric acid solution. The resulting mixture was concentrated under reduced pressure, and residue was then extracted with methylene chloride. An organic phase was dried over anhydrous sodium sulfate, filtered, and then concentrated under reduced pressure to give 10.0 g of 4-furan-2-yl-2,4-dioxo-butyric acid ethyl ester. This concentrate was used in the next steps without further purification.

$^1$H-NMR (acetone-$d_6$, 200 MHz), ppm($\delta$): 8.02~7.99 (m, 1H), 7.62~7.55 (m, 1H), 6.98~6.94 (m, 1H), 6.83~6.77 (m, 1H), 4.40 (q, 2H), 1.38 (t, 3H)

2) Step 2: Preparation of 5-furan-2-yl-isoxazole-3-carboxylic acid ethyl ester A suspension of 4-furan-2-yl-2,4-dioxo-butyric acid ethyl (10.0 g) and hydroxylamine hydrochloride salt in EtOH was stirred at 85° C. for 2 hours, and the resulting mixture was concentrated under reduced pressure. The concentrate was dissolved in methylene chloride and distilled water, and an organic phase was separated. The organic phase was dried over anhydrous sodium sulfate, filtered through silica gel pad, and then concentrated under reduced pressure to give 8.01 g of 5-furan-2-yl-isoxazole-3-carboxylic acid ethyl ester (yield: 77%). This concentrate was used in the next steps without further purification.

$^1$H-NMR (acetone-$d_6$, 200 MHz), ppm($\delta$): 7.90~7.86 (m, 1H), 7.20 (d, 1H), 7.00 (s, 1H), 6.77~6.73 (n 1H), 4.45 (q, 2H), 1.41 (t, 3H)

3) Step 3: Preparation of 5-furan-2-yl-isoxazole-3-carboxylic acid

To a solution of 5-furan-2-yl-isoxazole-3-carboxylic acid ethyl ester (4.14 g) in THF (130 mL) and methanol (25 mL) was slowly added 1N lithium hydroxide aqueous solution (80 mL). The resulting mixture was stirred for 15 hours, and then concentrated under reduced pressure. The remaining solution was acidified with 1N hydrochloric acid to form a solid, and the solid was filtered, washed with distilled water, dried to give 3.22 g of 5-furan-2-yl-isoxazole-3-carboxylic acid (yield: 90%) as a white solid.

$^1$H-NMR (acetone-$d_6$, 200 MHz), ppm($\delta$): 7.90~7.86 (m, 1H), 7.19 (d, 1H), 7.00 (s, 1H), 6.77~6.73 (m, 1H)

4) Step 4: Preparation of 5-furan-2-yl-isoxazole-3-carboxylic acid (3-imidazol-1-yl-propyl)-amide (derivative 1)

To a solution of 5-furan-2-yl-isoxazole-3-carboxylic acid (7 mg) and 3-imidazol-1-yl-propylamine (0.005 mL) in DMF were added HOBt (8 mg), EDC (9 mg) and TEA (0.014 mL). The resulting solution was stirred at a room temperature for 18 hours, and then concentrated under reduced pressure. The resulting concentrate was purified with preparative HPLC to give 4 mg of 5-furan-2-yl-isoxazole-3-carboxylic acid (3-imidazol-1-yl-propyl)-amide (yield: 35%).

1H-NMR (acetone-$d_6$, 200 MHz), ppm($\delta$): 8.16 (bs, 1H), 7.86~7.84 (m, 1H), 7.65~7.61 (m, 1H), 7.19~7.12 (m, 2H), 6.97~6.89 (m, 2H), 6.78~6.71 (m, 1H), 4.18 (t, 2H), 3.48 (q, 2H), 2.24~2.07 (m, 2H) Exact Mass (calc.): 286.11 LC-MS (ESI+) m/e (M+1)+: 287

The following derivatives 2 to 70 were prepared in the same manner as in the synthesis of the isoxazole derivative 1, except for the use of suitable starting material. The NMR results are listed in the following Table 1.

TABLE 1

| No. | Chemical Structure | NMR Results |
|---|---|---|
| 1 | 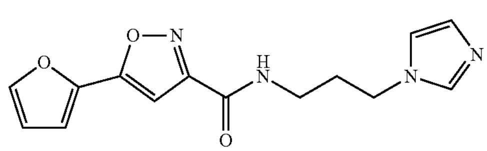 [SMILES: O=C(NCCCn1ccnc1)c1cc(-c2ccco2)on1] | 1H-NMR (acetone-$d_6$, 200 MHz), ppm ($\delta$): 8.16 (bs, 1H), 7.86~7.84 (m, 1H), 7.65~7.61 (m, 1H), 7.19~7.12 (m, 2H), 6.97~6.89 (m, 2H), 6.78~6.71 (m, 1H), 4.18 (t, 2H), 3.48 (q, 2H), 2.24~2.07 (m, 2H) Exact Mass (calc.): 286.11 LC-MS (ESI+) m/e (M + 1)+: 287 |
| 2 | 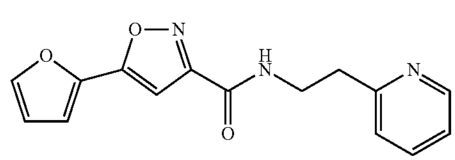 [SMILES: O=C(NCCc1ccccn1)c1cc(-c2ccco2)on1] | $^1$H-NMR (acetone-$d_6$, 200 MHz), ppm ($\delta$): 8.78~8.06 (m, 2H), 8.00~7.53 (m, 2H), 7.50~6.60 (m, 5H), 3.83 (q, 2H), 3.14 (t, 2H) Exact Mass (calc.): 283.10 LC-MS (ESI+) m/e (M + 1)$^+$: 284 |

TABLE 1-continued

| No. | Chemical Structure | NMR Results |
|---|---|---|
| 3 | 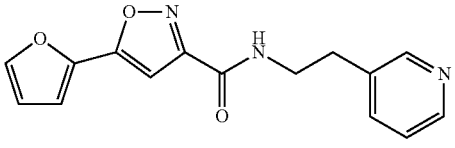 [SMILES: O=C(NCCc1cccnc1)c1cc(-c2ccco2)on1] | ¹H-NMR (acetone-d₆, 200 MHz), ppm (δ): 8.56~8.42 (m, 2H), 8.09 (bs, 1H), 7.88~7.84 (m, 1H), 7.75~7.67 (m, 1H), 7.35~7.26 (m, 1H), 7.18~7.13 (m, 1H), 6.91 (s, 1H), 6.76~6.71 (m, 1H), 3.73 (q, 2H), 3.02 (t, 2H)<br>Exact Mass (calc.): 283.10 LC-MS (ESI+) m/e (M + 1)⁺: 284 |
| 4 | 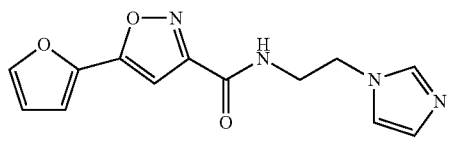 | ¹H-NMR (acetone-d₆, 200 MHz), ppm (δ): 8.20 (bs, 1H), 7.91~7.84 (m, 1H), 7.63~7.54 (m, 1H), 7.22~7.12 (m, 2H), 6.98~6.88 (m, 2H), 6.78~6.70 (m, 1H), 4.34 (t, 2H), 3.82 (q, 2H)<br>Exact Mass (calc.): 272.09 LC-MS (ESI+) m/e (M + 1)⁺: 273 |
| 5 | 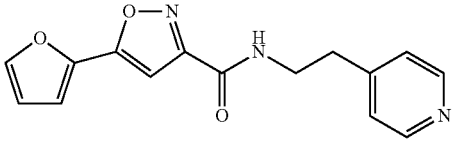 [SMILES: O=C(NCCc1ccncc1)c1cc(-c2ccco2)on1] | ¹H-NMR (acetone-d₆, 200 MHz), ppm (δ): 8.53~8.48 (m, 2H), 8.05 (bs, 1H), 7.88~7.83 (m, 1H), 7.33~7.25 (m, 2H), 7.17~7.14 (m, 1H), 6.91 (s, 1H), 6.75~6.70 (m, 1H), 3.75 (q, 2H), 3.02 (t, 2H)<br>Exact Mass (calc.): 283.10 LC-MS (ESI+) m/e (M + 1)⁺: 284 |
| 6 | 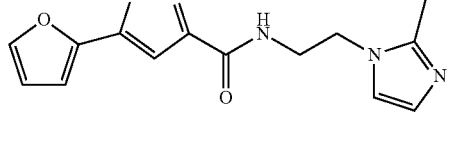 | ¹H-NMR (acetone-d₆, 200 MHz), ppm (δ): 8.25 (bs, 1H), 7.88~7.85 (m, 1H), 7.18~7.16 (m, 1H), 7.02~6.97 (m, 1H), 6.93 (s, 1H), 6.76~6.71 (m, 2H), 4.21 (t, 2H), 3.77 (q, 2H), 2.34 (s, 3H)<br>Exact Mass (calc.): 286.11 LC-MS (ESI+) m/e (M + 1)⁺: 287 |
| 7 | 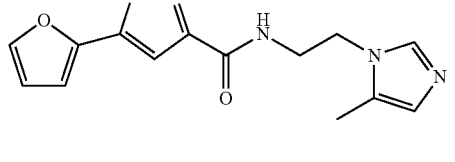 | ¹H-NMR (acetone-d₆, 200 MHz), ppm (δ): 8.22 (bs, 1H), 7.89~7.84 (m, 1H), 7.45~7.38 (m, 1H), 7.19~7.13 (m, 1H), 6.93 (s, 1H), 6.76~6.71 (m, 1H), 6.65~6.61 (m, 1H), 4.24 (t, 2H), 3.74 (q, 2H), 2.25 (s, 3H)<br>Exact Mass (calc.): 286.11 LC-MS (ESI+) m/e (M + 1)⁺: 287 |
| 8 | 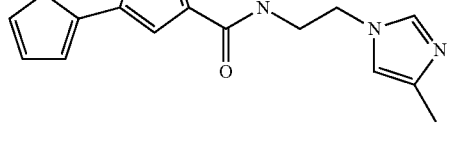 | ¹H-NMR (acetone-d₆, 200 MHz), ppm (δ): 8.22 (bs, 1H), 7.89~7.84 (m, 1H), 7.45~7.38 (m, 1H), 7.19~7.13 (m, 1H), 6.93 (s, 1H), 6.86~6.82 (m, 1H), 6.76~6.71 (m, 1H), 4.24 (t, 2H), 3.74 (q, 2H), 2.10 (s, 3H)<br>Exact Mass (calc.): 286.11 LC-MS (ESI+) m/e (M + 1)⁺: 287 |
| 9 | 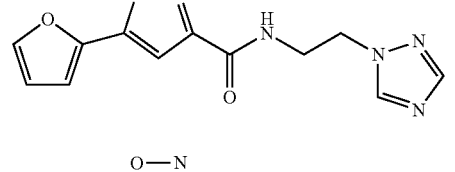 | ¹H-NMR (acetone-d₆, 200 MHz), ppm (δ): 8.40 (s, 1H), 8.20 (bs, 1H), 7.91~7.83 (m, 2H), 7.18~7.16 (m, 1H), 6.92 (s, 1H), 6.76~6.71 (m, 1H), 4.54 (t, 2H), 3.90 (q, 2H)<br>Exact Mass (calc.): 273.09 LC-MS (ESI+) m/e (M + 1)⁺: 274 |
| 10 | 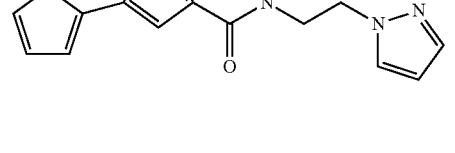 | 1H-NMR (acetone-d6, 200 MHz), ppm (δ): 8.14 (bs, 1H), 7.89~7.85 (m, 1H), 7.71~7.66 (m, 1H), 7.49~7.44 (m, 1H), 7.19~7.14 (m, 1H), 6.93 (s, 1H), 6.76~6.72 (m, 1H), 6.28~6.22 (m, 1H), 4.45 (t, J = 5.80, 2H), 3.92~3.81 (m, 2H)<br>Exact Mass (calc.): 272.26 LC-MS (ESI+) m/e (M + 1)+: 273 |
| 11 | 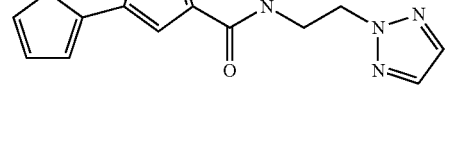 | 1H-NMR (acetone-d6, 200 MHz), ppm (δ): 8.13 (bs, 1H), 7.89~7.84 (m, 1H), 7.71 (s, 2H), 7.19~7.14 (m, 1H), 6.92 (s, 1H), 6.76~6.72 (m, 1H), 4.74 (t, J = 5.80, 2H), 4.01~3.90 (m, 2H)<br>Exact Mass (calc.): 273.25 LC-MS (ESI+) m/e (M + 1)+: 274 |

TABLE 1-continued

| No. | Chemical Structure | NMR Results |
|---|---|---|
| 12 | 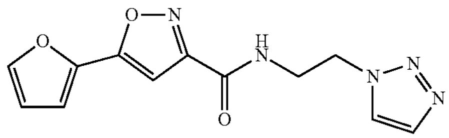 [SMILES: O=C(NCCn1ccnn1)c1cc(-c2ccco2)on1] | $^1$H-NMR (acetone-$d_6$, 200 MHz), ppm ($\delta$):<br>8.20 (bs, 1H), 8.03s, 1H), 7.89~7.84 (m, 1H),<br>7.67 (s, 1H), 7.19~7.14 (m, 1H), 6.92 (s, 1H),<br>6.76~6.72 (m, 1H), 4.74 (t, J = 5.80, 2H),<br>4.01~3.91 (m, 2H)<br>Exact Mass (calc.): 273.25 LC-MS (ESI+) m/e<br>(M + 1)+: 274 |
| 13 | 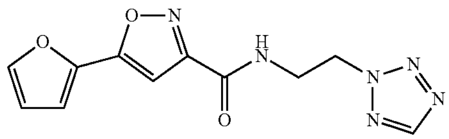 [SMILES: O=C(NCCn1ncnn1)c1cc(-c2ccco2)on1] | $^1$H-NMR (acetone-$d_6$, 200 MHz), ppm ($\delta$):<br>8.74 (s, 1H), 8.24 (bs, 1H), 7.89~7.85 (m,<br>1H), 7.19~7.14 (m, 1H), 6.91 (s, 1H),<br>6.76~6.72 (m, 1H), 5.02 (t, J = 5.80, 2H),<br>4.25~3.99 (m, 2H)<br>Exact Mass (calc.): 274.24 LC-MS (ESI+) m/e<br>(M + 1)+: 275 |
| 14 | 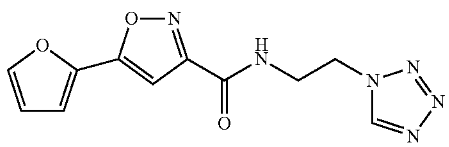 [SMILES: O=C(NCCn1cnnn1)c1cc(-c2ccco2)on1] | $^1$H-NMR (DMSO-$d_6$, 200 MHz), ppm ($\delta$): 9.41 (s,<br>1H), 9.04 (t, J = 5.40, 1H), 8.01~7.94 (m,<br>1H), 7.38~7.23 (m, 1H), 7.03 (s, 1H),<br>6.78~6.72 (m, 1H), 4.66 (t, J = 5.40, 2H),<br>3.72 (q, J = 5.40, 2H)<br>Exact Mass (calc.): 274.24 LC-MS (ESI+) m/e<br>(M + 1)+: 275 |
| 15 | 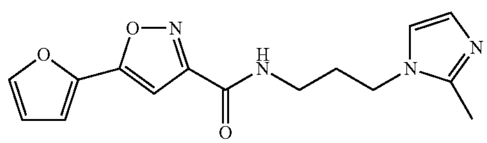 | $^1$H-NMR (acetone-$d_6$, 200 MHz), ppm ($\delta$):<br>8.15 (bs, 1H), 7.89~7.80 (m, 1H),<br>7.19~7.14 (m, 1H), 7.10~7.04 (m, 1H),<br>6.94 (s, 1H), 6.79~6.71 (m, 2H), 4.06 (t,<br>J = 6.00, 2H), 3.57~3.43 (m, 2H), 2.33 (s,<br>3H), 2.19~2.07 (m, 2H)<br>Exact Mass (calc.): 300.32 LC-MS (ESI+) m/e<br>(M + 1)+: 301 |
| 16 | 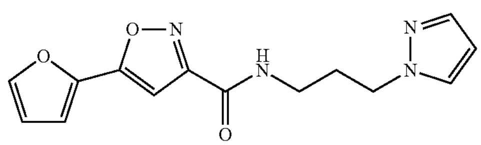 [SMILES: O=C(NCCCn1cccn1)c1cc(-c2ccco2)on1] | $^1$H-NMR (acetone-$d_6$, 200 MHz), ppm ($\delta$):<br>8.08 (bs, 1H), 7.89~7.84 (m, 1H),<br>7.74~7.67 (m, 1H), 7.47~7.42 (m, 1H),<br>7.19~7.14 (m, 1H), 6.93 (s, 1H),<br>6.76~6.71 (m, 1H), 6.26~6.22 (m, 1H),<br>4.30 (t, J = 7.00, 2H), 3.52~3.40 (m, 2H),<br>2.27~2.11 (m, 2H)<br>Exact Mass (calc.): 286.29 LC-MS (ESI+) m/e<br>(M + 1)+: 287 |
| 17 | 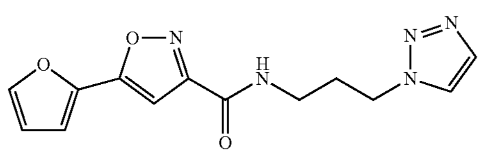 [SMILES: O=C(NCCCn1ccnn1)c1cc(-c2ccco2)on1] | $^1$H-NMR (DMSO-$d_6$, 200 MHz), ppm ($\delta$): 8.92 (bs,<br>1H), 8.16~8.12 (m, 1H), 7.98~7.94 (m, 1H),<br>7.71~7.67 (m, 1H), 7.25~7.20 (m, 1H),<br>7.04 (s, 1H), 6.79~6.71 (m, 1H), 4.41 (t,<br>J = 6.00, 2H), 3.27~3.21 (m, 2H),<br>2.10~2.02 (m, 2H)<br>Exact Mass (calc.): 287.28 LC-MS (ESI+) m/e<br>(M + 1)+: 288 |
| 18 | 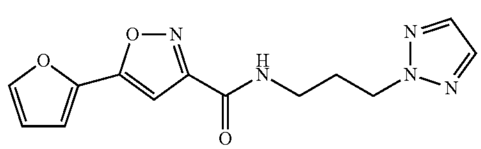 [SMILES: O=C(NCCCn1nccn1)c1cc(-c2ccco2)on1] | $^1$H-NMR (DMSO-$d_6$, 200 MHz), ppm ($\delta$):<br>9.00~8.95 (m, 1H), 7.98 (s, 1H), 7.77 (s,<br>1H), 7.23 (m, 1H), 7.04 (s, 1H), 6.74 (m, 1H),<br>4.47 (t, 2H), 3.29~3.25 (m, 2H),<br>2.20~2.05 (m, 2H)<br>Exact Mass(calc.): 287.10 LC-MS (ESI+) m/e<br>(M + 1)+: 288 |
| 19 | 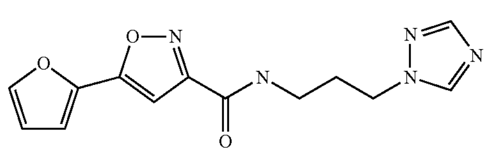 [SMILES: O=C(NCCCn1cncn1)c1cc(-c2ccco2)on1] | $^1$H-NMR (DMSO-$d_6$, 200 MHz), ppm ($\delta$):<br>9.00~8.95 (m, 1H), 8.51 (s, 1H), 7.97 (m,<br>2H), 7.24 (m, 1H), 7.06 (s, 1H), 6.75 (m, 1H),<br>4.23 (t, 2H), 3.30~3.20 (m, 2H),<br>2.10~2.04 (m, 2H)<br>Exact Mass (calc.): 287.10 LC-MS (ESI+) m/e<br>(M + 1)+: 288 |
| 20 | 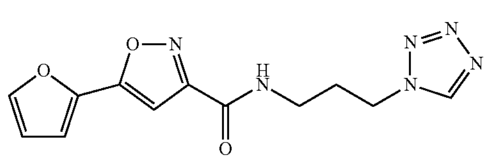 [SMILES: O=C(NCCCn1cnnn1)c1cc(-c2ccco2)on1] | $^1$H-NMR (DMSO-$d_6$, 200 MHz), ppm ($\delta$): 9.39 (s,<br>1H), 9.00~8.95 (m, 1H), 7.97 (s, 1H),<br>7.23 (m, 1H), 7.05 (s, 1H), 6.74 (m, 1H),<br>4.50 (t, 2H), 3.29~3.25 (m, 2H),<br>2.15~2.08 (m, 2H)<br>Exact Mass (calc.): 288.10 LC-MS (ESI+) m/e<br>(M + 1)+: 289 |

TABLE 1-continued

| No. | Chemical Structure | NMR Results |
|---|---|---|
| 21 | 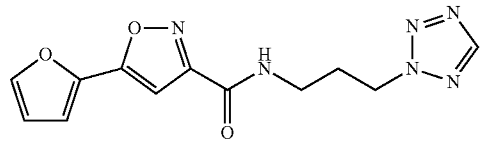 [SMILES: O=C(NCCCn1ncnn1)c1cc(-c2ccco2)on1] | $^1$H-NMR (DMSO-d$_6$, 200 MHz), ppm (δ): 8.96 (m, 2H), 7.97 (s, 1H), 7.24 (s, 1H), 7.06 (s, 1H), 6.80~6.70 (m, 1H), 4.80~4.64 (m, 2H), 3.29~3.25 (m, 2H), 2.22~2.05 (m, 2H) Exact Mass (calc.): 288.10 LC-MS (ESI+) m/e (M + 1)+: 289 |
| 22 | 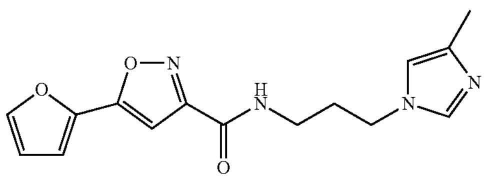 [SMILES: Cc1cn(CCCNC(=O)c2cc(-c3ccco3)on2)cn1] | $^1$H-NMR (acetone-d$_6$, 200 MHz), ppm (δ): 8.18 (bs, 1H), 7.89~7.84 (m, 1H), 7.19~7.14 (m, 1H), 7.09~7.04 (m, 1H), 6.94 (s, 1H), 6.79~6.71 (m, 2H), 4.06 (t, J = 7.40, 2H), 3.57~3.43 (m, 2H), 2.32 (s, 3H), 2.21~2.07 (m, 2H); Exact Mass (calc.): 300.32 LC-MS (ESI+) m/e (M + 1)+: 301 |
| 23 | 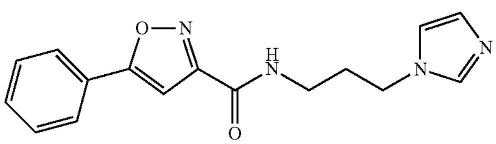 [SMILES: O=C(NCCCn1ccnc1)c1cc(-c2ccccc2)on1] | $^1$H-NMR (acetone-d$_6$, 200 MHz), ppm (δ): 8.17 (bs, 1H), 8.01~7.92 (m, 2H), 7.69~7.53 (m, 4H), 7.24~7.17 (m, 2H), 7.01~6.73 (m, 1H), 4.19 (t, 2H), 3.47 (q, 2H), 2.24~2.06 (m, 2H) Exact Mass (calc.): 296.13 LC-MS (ESI+) m/e (M + 1)$^+$: 297 |
| 24 | 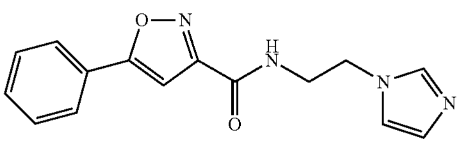 [SMILES: O=C(NCCn1ccnc1)c1cc(-c2ccccc2)on1] | NMR (acetone-d6, 200 MHz), ppm (δ): 8.15 (bs, 1H), 7.99~7.91 (m, 2H), 7.62~7.50 (m, 4H), 7.19~7.12 (m, 2H), 6.93~6.86 (m, 1H), 4.34 (t, J = 5.80, 2H), 3.87~3.77 (m, 2H) Exact Mass (calc.): 282.30 LC-MS (ESI+) m/e (M + 1)+: 283 |
| 25 | 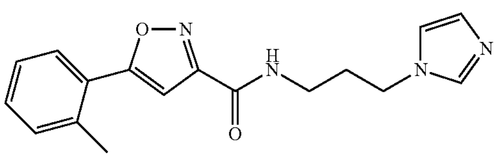 [SMILES: Cc1ccccc1-c1cc(C(=O)NCCCn2ccnc2)no1] | $^1$H-NMR (acetone-d$_6$, 200 MHz), ppm (δ): 8.12 (bs, 1H), 7.83~7.76 (m, 1H), 7.66~7.62 (m, 1H), 7.48~7.36 (m, 3H), 7.22~7.18 (m, 1H), 7.01~6.93 (m, 2H), 4.19 (t, 2H), 3.50 (q, 2H), 2.56 (s, 3H), 2.25~2.13 (m, 2H) Exact Mass (calc.): 310.14 LC-MS (ESI+) m/e (M + 1)$^+$: 311 |
| 26 | 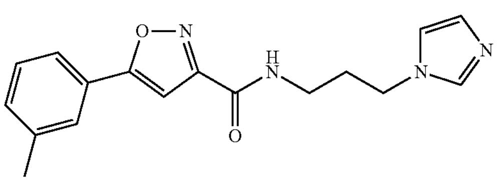 [SMILES: Cc1cccc(-c2cc(C(=O)NCCCn3ccnc3)no2)c1] | $^1$H-NMR (acetone-d$_6$, 200 MHz), ppm (δ): 8.15 (bs, 1H), 7.82~7.62 (m, 3H), 7.52~7.34 (m, 2H), 7.23~7.15 (m, 2H), 6.98~6.74 (m, 1H), 4.19 (t, 2H), 3.49 (q, 2H), 2.45 (s, 3H), 2.43~2.05 (m, 2H) Exact Mass (calc.): 310.14 LC-MS (ESI+) m/e (M + 1)$^+$: 311 |
| 27 | 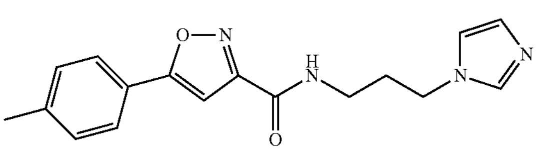 [SMILES: Cc1ccc(-c2cc(C(=O)NCCCn3ccnc3)no2)cc1] | $^1$H-NMR (acetone-d$_6$, 200 MHz), ppm (δ): 8.10 (bs, 1H), 7.88~7.81 (m, 2H), 7.66~7.62 (m, 1H), 7.45~7.36 (m, 2H), 7.22~7.17 (m, 1H), 7.11 (s, 1H), 6.95~6.40 (m, 1H), 4.18 (t, 2H), 3.48 (q, 2H), 2.43 (s, 3H), 2.25~2.03 (m, 2H) Exact Mass (calc.): 310.14 LC-MS (ESI+) m/e (M + 1)$^+$: 311 |
| 28 | 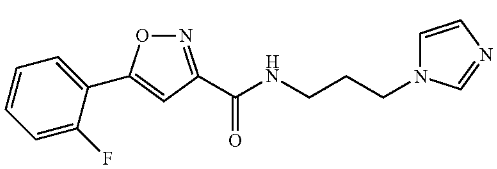 [SMILES: O=C(NCCCn1ccnc1)c1cc(-c2ccccc2F)on1] | $^1$H-NMR (acetone-d$_6$, 200 MHz), ppm (δ): 8.25~7.96 (m, 2H), 7.72~7.35 (m, 4H), 7.26~6.91 (m, 3H), 4.20 (t, 2H), 3.50 (q, 2H), 2.24~2.07 (m, 2H) Exact Mass (calc.): 314.12 LC-MS (ESI+) m/e (M + 1)$^+$: 315 |
| 29 | 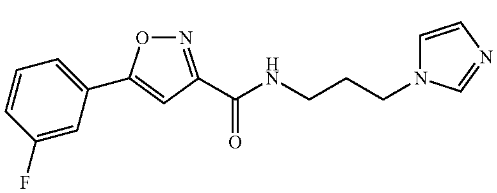 [SMILES: O=C(NCCCn1ccnc1)c1cc(-c2cccc(F)c2)on1] | $^1$H-NMR (acetone-d$_6$, 200 MHz), ppm (δ): 8.26~7.06 (m, 1H), 7.9~7.54 (m, 4H), 7.44~7.12 (m, 3H), $^1$H-NMR (acetone-d6, 200 MHz), ppm (δ): 7.06~6.76 (m, 1H), 4.20 (t, 2H), 3.50 (q, 2H), 2.24~2.07 (m, 2H) Exact Mass (calc.): 314.12 LC-MS (ESI+) m/e (M + 1)$^+$: 315 |

TABLE 1-continued

| No. | Chemical Structure | NMR Results |
|---|---|---|
| 30 | 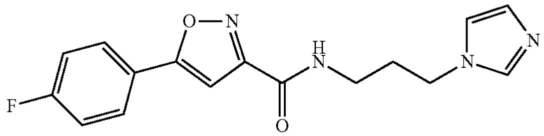 [SMILES: O=C(NCCCn1ccnc1)c1cc(-c2ccc(F)cc2)on1] | $^1$H-NMR (acetone-$d_6$, 200 MHz), ppm (δ): 8.21~7.95 (m, 2H), 7.67~7.58 (m, 1H), 7.44~7.28 (m, 2H), 7.24~7.12 (m, 1H), 6.94 (s, 1H), 4.17 (t, 2H), 3.48 (q, 2H), 2.23~2.06 (m, 2H)<br>Exact Mass (calc.): 314.12 LC-MS (ESI+) m/e (M + 1)$^+$: 315 |
| 31 | 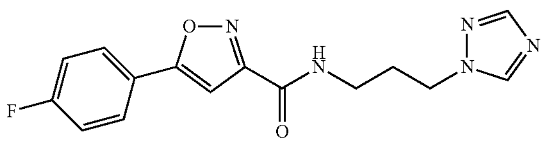 [SMILES: O=C(NCCCn1cncn1)c1cc(-c2ccc(F)cc2)on1] | $^1$H-NMR (DMSO-$d_6$, 200 MHz), ppm (δ): 8.97~8.92 (m, 1H), 8.51 (s, 1H), 8.02~7.95 (m, 3H), 7.43~7.34 (m, 3H), 4.21 (t, 2H), 3.29~.322 (m, 2H), 2.02 (m, 2H)<br>Exact Mass (calc.): 315.11 LC-MS (ESI+) m/e (M + 1)+: 316 |
| 32 | 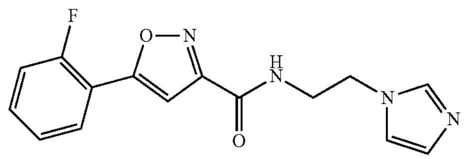 [SMILES: O=C(NCCn1ccnc1)c1cc(-c2ccccc2F)on1] | $^1$H-NMR (acetone-$d_6$, 200 MHz), ppm (δ): 8.26 (bs, 1H), 8.07~7.96 (m, 1H), 7.72~7.35 (m, 4H), 7.19~7.04 (m, 2H), 6.92 (s, 1H), 4.35 (t, J = 6.00, 2H), 3.88~3.76 (m, 2H)<br>Exact Mass (calc.): 300.29 LC-MS (ESI+) m/e (M + 1)+: 301 |
| 33 | 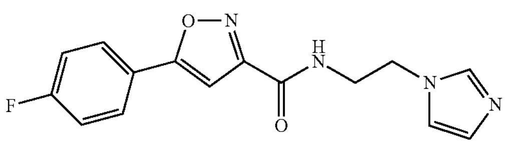 [SMILES: O=C(NCCn1ccnc1)c1cc(-c2ccc(F)cc2)on1] | $^1$H-NMR (acetone-$d_6$, 200 MHz), ppm (δ): 8.15 (bs, 1H), 8.09~7.96 (m, 2H), 7.57 (s, 1H), 7.44~7.30 (m, 2H), 7.19~7.08 (m, 2H), 6.92 (s, 1H), 4.34 (t, J = 5.80, 2H), 3.88~3.75 (m, 2H)<br>Exact Mass (calc.): 300.29 LC-MS (ESI+) m/e (M + 1)+: 301 |
| 34 | 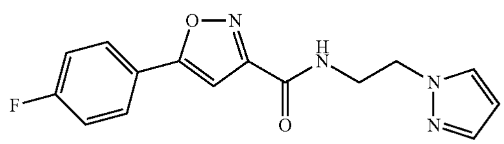 [SMILES: O=C(NCCn1cccn1)c1cc(-c2ccc(F)cc2)on1] | $^1$H-NMR (DMSO-$d_6$, 200 MHz), ppm (δ): 8.95 (m, 1H), 7.99 (m, 2H), 7.70 (s, 1H), 7.44~7.34 (m, 4H), 6.22 (m, 1H), 4.31 (t, 2H), 3.65 (m, 2H)<br>Exact Mass (calc.): 300.10 LC-MS (ESI+) m/e (M + 1)+: 301 |
| 35 | 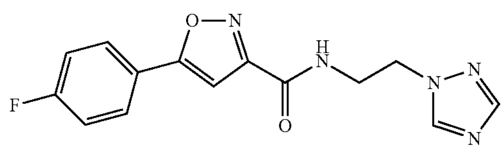 [SMILES: O=C(NCCn1cncn1)c1cc(-c2ccc(F)cc2)on1] | $^1$H-NMR (DMSO-$d_6$, 200 MHz), ppm (δ): 8.43 (m, 1H), 8.20 (br, 1H), 8.06~7.99 (m, 2H), 7.91 (m, 1H), 7.41~7.33 (2H, m), 7.17 (m, 1H), 4.55 (m, 2H), 3.93 (m, 2H)<br>Exact Mass (calc.): 301.10 LC-MS (ESI+) m/e (M + 1)+: 302 |
| 36 | 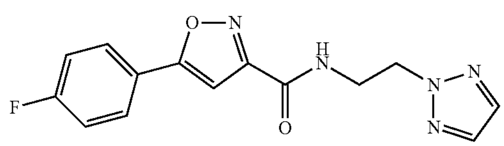 [SMILES: O=C(NCCn1nccn1)c1cc(-c2ccc(F)cc2)on1] | $^1$H-NMR (DMSO-$d_6$, 200 MHz), ppm (δ): 8.95 (br, 1H), 8.05~7.95 (m, 2H), 7.78 (s, 2H), 7.50~7.34 (m, 3H), 4.61 (t, 2H), 3.78~3.62 (m, 2H)<br>Exact Mass (calc.): 301.10 LC-MS (ESI+) m/e (M + 1)+: 302 |
| 37 | 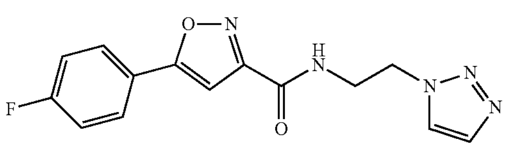 [SMILES: O=C(NCCn1ccnn1)c1cc(-c2ccc(F)cc2)on1] | $^1$H-NMR (DMSO-$d_6$, 200 MHz), ppm (δ): 8.95 (m, 1H), 8.11 (s, 1H), 8.00~7.96 (m, 2H), 7.71 (s, 1H), 7.45~7.34 (m, 3H), 4.59 (t, 2H), 3.78~3.62 (m, 2H)<br>Exact Mass (calc.): 301.10 LC-MS (ESI+) m/e (M + 1)+: 302 |
| 38 | 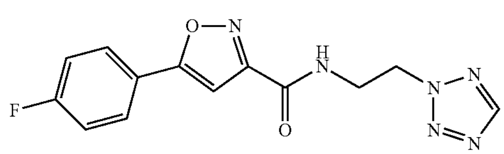 [SMILES: O=C(NCCn1ncnn1)c1cc(-c2ccc(F)cc2)on1] | $^1$H-NMR (DMSO-$d_6$, 200 MHz), ppm (δ): 8.96 (m, 2H), 8.02~7.94 (m, 2H), 7.45~7.33 (m, 3H), 4.90 (t, 2H), 3.85~3.73 (m, 2H)<br>Exact Mass (calc.): 302.09 LC-MS (ESI+) m/e (M+ 1)+: 303 |
| 39 | 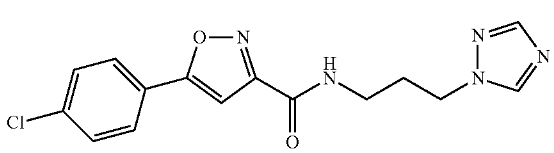 [SMILES: O=C(NCCCn1cncn1)c1cc(-c2ccc(Cl)cc2)on1] | $^1$H-NMR (DMSO-$d_6$, 200 MHz), ppm (δ): 8.90 (m, 1H), 8.49 (s, 1H), 7.95~7.91 (m, 3H), 7.62~7.58 (m, 2H), 7.39 (s, 1H), 4.20 (t, 2H), 3.29~3.25 (m, 2H), 2.05~1.98 (m, 2H)<br>Exact Mass (calc.): 331.08 LC-MS (ESI+) m/e (M + 1)+: 332 |

TABLE 1-continued

| No. | Chemical Structure | NMR Results |
|---|---|---|
| 40 | 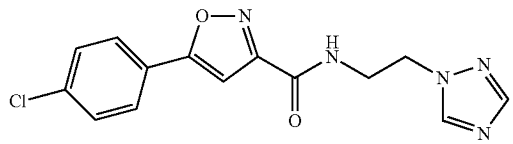 [SMILES: O=C(NCCn1cncn1)c1cc(-c2ccc(Cl)cc2)on1] | $^1$H-NMR (DMSO-$d_6$, 200 MHz), ppm (δ): 8.95~8.84 (m, 1H), 8.46 (s, 1H), 7.95~7.91 (m, 3H), 7.62~7.58 (m, 2H), 7.36 (s, 1H), 4.36 (m, 2H), 3.66 (m, 2H)<br>Exact Mass (calc.): 317.07 LC-MS (ESI+) m/e (M + 1)+: 318 |
| 41 | 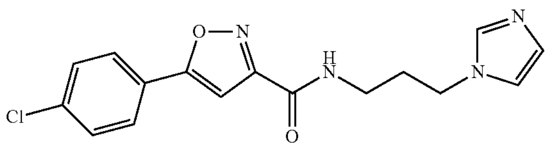 [SMILES: O=C(NCCCn1ccnc1)c1cc(-c2ccc(Cl)cc2)on1] | $^1$H-NMR (DMSO-$d_6$, 500 MHz), ppm (δ): 9.00 (t, 1H), 7.97 (m, 2H), 7.66 (m, 2H), 7.44 (s, 1H), 7.22 (s, 1H), 6.90 (s, 1H) 4.03 (t, 2H), 3.31 (q, 2H), 2.00 (q, 2H)<br>Exact Mass (calc.): 330.09 LC-MS (ESI+) m/e (M + 1)+: 331 |
| 42 | 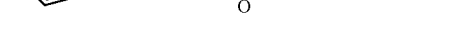 | $^1$H-NMR (acetone-$d_6$, 200 MHz), ppm (δ): 8.27~7.81 (m, 2H), 7.77~7.42 (m, 2H), 7.40~6.82 (m, 5H), 4.11 (t, 2H), 4.05 (s, 3H), 3.48 (q, 2H), 2.23~2.02 (m, 2H)<br>Exact Mass (calc.): 326.14 LC-MS (ESI+) m/e (M + 1)$^+$: 327 |
| 43 | 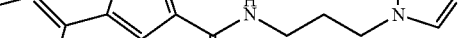 | $^1$H-NMR (acetone-$d_6$, 200 MHz), ppm (δ): 8.23 (bs, 1H), 7.79~6.89 (m, 8H), 4.24 (t, 2H), 3.91 (s, 3H), 3.47 (q, 2H), 2.39~2.12 (m, 2H)<br>Exact Mass (calc.): 326.14 LC-MS (ESI+) m/e (M + 1)$^+$: 327 |
| 44 | 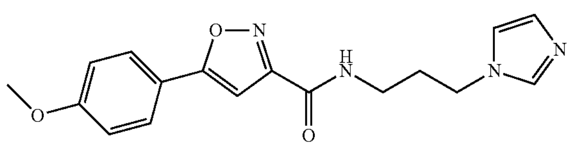 [SMILES: COc1ccc(-c2cc(C(=O)NCCCn3ccnc3)no2)cc1] | $^1$H-NMR (acetone-$d_6$, 200 MHz), ppm (δ): 8.32~7.42 (m, 4H), 7.38~6.90 (m, 5H), 4.19 (t, 2H), 3.96 (s, 3H), 3.46 (q, 2H), 2.39~2.02 (m, 2H)<br>Exact Mass (calc.): 326.14 LC-MS (ESI+) m/e (M + 1)$^+$: 327 |
| 45 | 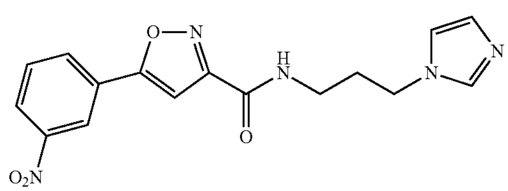 | $^1$H-NMR (acetone-$d_6$, 200 MHz), ppm (δ): 8.18~8.96 (m, 2H), 7.85~7.54 (m, 5H), 7.19 (s, 1H), 6.96~6.88 (m, 1H), 4.21 (t, 2H), 3.42 (q, 2H), 2.21~2.06 (m, 2H)<br>Exact Mass (calc.): 341.11 LC-MS (ESI+) m/e (M + 1)$^+$: 342 |
| 46 | 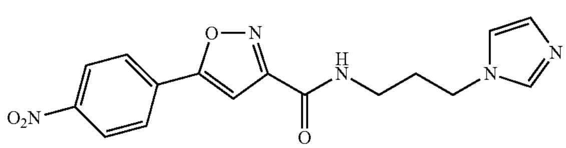 [SMILES: O=C(NCCCn1ccnc1)c1cc(-c2ccc([N+](=O)[O-])cc2)on1] | $^1$H-NMR (acetone-$d_6$, 200 MHz), ppm (δ): 8.50~8.05 (m, 5H), 7.66~7.45 (m, 2H), 7.21~7.17 (m, 1H), 6.94 (s, 1H), 4.19 (t, 2H), 3.49 (q, 2H), 2.22~2.00 (m, 2H)<br>Exact Mass (calc.): 341.11 LC-MS (ESI+) m/e (M + 1)$^+$: 342 |
| 47 | 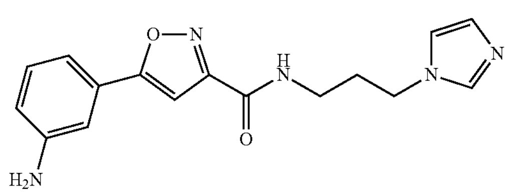 [SMILES: Nc1cccc(-c2cc(C(=O)NCCCn3ccnc3)no2)c1] | $^1$H-NMR (acetone-$d_6$, 200 MHz), ppm (δ): 7.76~7.65 (m, 1H), 7.55~6.95 (m, 6H), 6.78~6.56 (m, 2H), 4.15 (t, 2H), 3.23 (q, 2H), 2.35~2.20 (m, 2H)<br>Exact Mass (calc.): 311.14 LC-MS (ESI+) m/e (M + 1)$^+$: 312 |
| 48 | 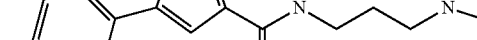 | $^1$H-NMR (acetone-$d_6$, 200 MHz), ppm (δ): 7.64~7.56 (m, 1H), 7.35~7.26 (m, 1H), 7.18~7.02 (m, 3H), 6.92 (s, 1H), 6.74~6.56 (m, 3H), 4.09 (t, 2H), 3.21 (q, 2H), 2.22~1.99 (m, 2H)<br>Exact Mass (calc.): 311.14 LC-MS (ESI+) m/e (M + 1)$^+$: 312 |

TABLE 1-continued

| No. | Chemical Structure | NMR Results |
|---|---|---|
| 49 | 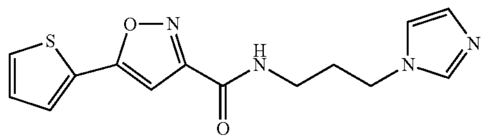 [SMILES: O=C(NCCCn1ccnc1)c1cc(-c2cccs2)on1] | $^1$H-NMR (acetone-$d_6$, 200 MHz), ppm (δ): 8.13 (bs, 1H), 7.84~7.66 (m, 2H), 7.66~7.61 (m, 1H), 7.32~7.26 (m, 1H), 7.21~7.18 (m, 1H), 7.03 (s, 1H), 6.77~6.72 (m, 1H), 4.18 (t, 2H), 3.48 (q, 2H), 2.24~2.06 (m, 2H) Exact Mass (calc.): 302.08 LC-MS (ESI+) m/e (M + 1)$^+$: 303 |
| 50 | 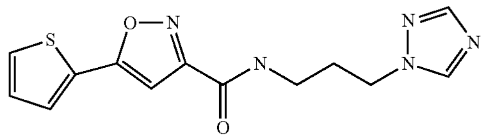 [SMILES: O=C(NCCCn1cncn1)c1cc(-c2cccs2)on1] | $^1$H-NMR (DMSO-$d_6$, 200 MHz), ppm (δ): 8.91 (m, 1H), 8.52 (s, 1H), 7.97 (s, 1H), 7.83 (m, 1H), 7.79 (m, 1H), 7.29~7.25 (m, 1H), 7.19 (s, 1H), 4.23 (t, 2H), 3.29~3.23 (m, 2H), 2.07~2.00 (m, 2H) Exact Mass (calc.): 303.08 LC-MS (ESI+) m/e (M + 1)+: 304 |
| 51 | 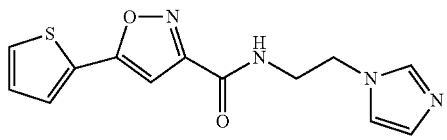 [SMILES: O=C(NCCn1ccnc1)c1cc(-c2cccs2)on1] | $^1$H-NMR (acetone-$d_6$, 200 MHz), ppm (δ): 8.15 (bs, 1H), 7.86~7.76 (m, 2H), 7.57 (s, 1H), 7.32~7.25 (m, 1H), 7.16~7.12 (m, 1H), 7.01 (s, 1H), 6.93~6.89 (m, 1H), 4.33 (t, J = 5.80, 2H), 3.88~3.76 (m, 2H) Exact Mass (calc.): 288.33 LC-MS (ESI+) m/e (M + 1)+: 289 |
| 52 | 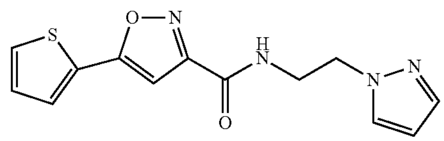 [SMILES: O=C(NCCn1cccn1)c1cc(-c2cccs2)on1] | $^1$H-NMR (acetone-$d_6$, 200 MHz), ppm (δ): 8.10 (bs, 1H), 7.86~7.76 (m, 2H), 7.72~7.66 (m, 1H), 7.49~7.46 (m, 1H), 7.33~7.26 (m, 1H), 7.02 (s, 1H), 6.27~6.23 (m, 1H), 4.44 (t, J = 5.80, 2H), 3.92~3.81 (m, 2H) Exact Mass (calc.): 288.33 LC-MS (ESI+) m/e (M + 1)+: 289 |
| 53 | 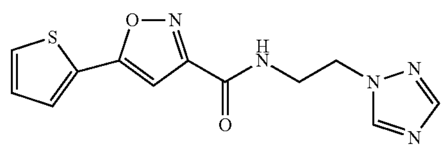 [SMILES: O=C(NCCn1cncn1)c1cc(-c2cccs2)on1] | $^1$H-NMR (acetone-$d_6$, 200 MHz), ppm (δ): 8.40 (s, 1H), 8.18 (bs, 1H), 7.90 (s, 1H), 7.84~7.76 (m, 2H), 7.32~7.26 (m, 1H), 7.01 (s, 1H), 4.54 (t, J = 5.40, 2H), 3.96~3.83 (m, 2H) Exact Mass (calc.): 289.32 LC-MS (ESI+) m/e (M + 1)+: 290 |
| 54 | 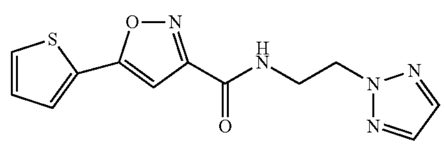 [SMILES: O=C(NCCn1nccn1)c1cc(-c2cccs2)on1] | $^1$H-NMR (acetone-$d_6$, 200 MHz), ppm (δ): 8.10 (bs, 1H), 7.85~7.76 (m, 2H), 7.71 (s, 2H), 7.32~7.26 (m, 1H), 7.02 (s, 1H), 4.74 (t, J = 5.80, 2H), 4.04~3.90 (m, 2H) Exact Mass (calc.): 289.32 LC-MS (ESI+) m/e (M + 1)+: 290 |
| 55 | 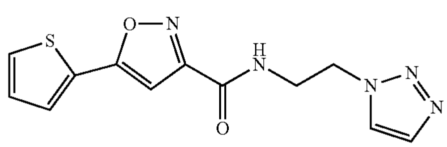 [SMILES: O=C(NCCn1ccnn1)c1cc(-c2cccs2)on1] | $^1$H-NMR (acetone-$d_6$, 200 MHz), ppm (δ): 8.19 (bs, 1H), 8.03 (s, 1H), 7.84~7.76 (m, 2H), 7.67 (s, 1H), 7.32~7.26 (m, 1H), 7.01 (s, 1H), 4.74 (t, J = 5.40, 2H), 4.01~3.88 (m, 2H) Exact Mass (calc.): 289.32 LC-MS (ESI+) m/e (M + 1)+: 290 |
| 56 | 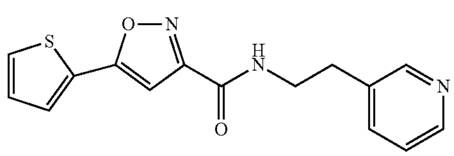 [SMILES: O=C(NCCc1cccnc1)c1cc(-c2cccs2)on1] | $^1$H-NMR (acetone-$d_6$, 200 MHz), ppm (δ): 8.53~8.42 (m, 2H), 8.07 (bs, 1H), 7.83~7.68 (m, 3H), 7.35~7.25 (m, 2H), 7.00 (s, 1H), 3.73 (q, 2H), 3.01 (t, 2H) Exact Mass (calc.): 299.07 LC-MS (ESI+) m/e (M + 1)$^+$: 300 |
| 57 | 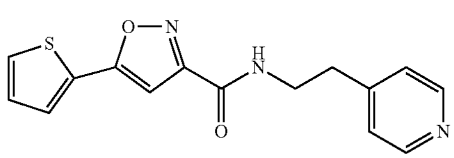 [SMILES: O=C(NCCc1ccncc1)c1cc(-c2cccs2)on1] | $^1$H-NMR (acetone-$d_6$, 200 MHz), ppm (δ): 8.53~8.43 (m, 2H), 8.08 (bs, 1H), 7.84~7.53 (m, 2H), 7.38~7.11 (m, 3H), 7.01 (s, 1H), 3.74 (q, 2H), 3.02 (t, 2H) Exact Mass (calc.): 299.07 LC-MS (ESI+) m/e (M + 1)$^+$: 300 |

TABLE 1-continued

| No. | Chemical Structure | NMR Results |
|---|---|---|
| 58 | 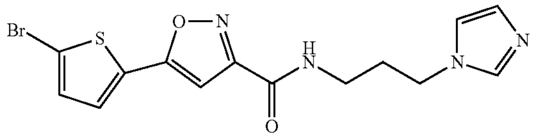 [SMILES: O=C(NCCCn1ccnc1)c1cc(-c2ccc(Br)s2)on1] | $^1$H-NMR (acetone-d$_6$, 200 MHz), ppm (δ): 8.15 (bs, 1H), 7.90~7.72 (m, 1H), 7.65~7.58 (m, 1H), 7.39~7.21 (m, 21H), 7.16~7.01 (m, 2H), 4.23 (t, 2H), 3.46 (q, 2H), 2.27~2.12 (m, 2H) Exact Mass (calc.): 379.99 LC-MS (ESI+) m/e (M + 1)$^+$: 381 |
| 59 | 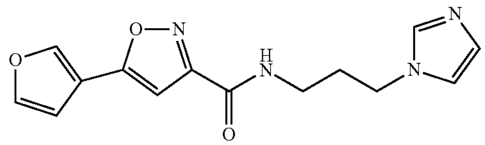 [SMILES: O=C(NCCCn1ccnc1)c1cc(-c2ccoc2)on1] | $^1$H-NMR (DMSO-d$_6$, 500 MHz), ppm (δ): 8.89 (m, 1H), 8.45 (s, 1H), 7.90 (m, 1H), 7.66 (m, 1H), 7.21 (s, 1H), 7.10 (s, 1H), 7.03 (m, 1H), 6.90 (s, 1H), 4.02 (t, 2H), 3.24 (q, 2H), 1.97 (quintet, 2H) Exact Mass (calc.): 286.11 LC-MS (ESI+) m/e (M + 1)+: 287 |
| 60 | 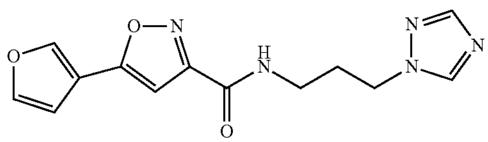 [SMILES: O=C(NCCCn1cncn1)c1cc(-c2ccoc2)on1] | $^1$H-NMR (DMSO-d$_6$, 500 MHz), ppm (δ): 8.91 (m, 1H), 8.54 (s, 1H), 8.46 (s, 1H), 7.98 (s, 1H), 7.90 (m, 1H), 7.10 (s, 1H), 7.03 (m, 1H), 4.24 (t, 2H), 3.26 (q, 2H), 2.05 (m, 2H) Exact Mass (calc.): 287.10 LC-MS (ESI+) m/e (M + 1)+: 288 |
| 61 | 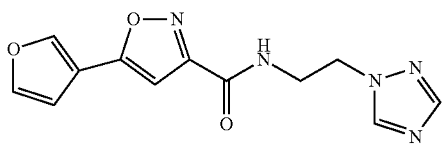 [SMILES: O=C(NCCn1cncn1)c1cc(-c2ccoc2)on1] | $^1$H-NMR (DMSO-d$_6$, 500 MHz), ppm (δ): 8.91 (m, 1H), 8.49 (s, 1H), 8.45 (s, 1H), 7.97 (s, 1H), 7.90 (m, 1H), 7.07 (s, 1H), 7.03 (m, 1H), 4.34 (t, 2H), 3.67 (q, 2H) Exact Mass (calc.): 273.09 LC-MS (ESI+) m/e (M + 1)+: 274 |
| 62 | 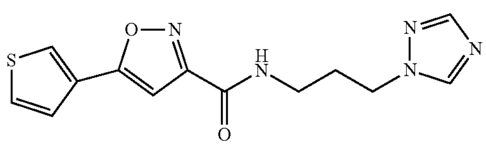 [SMILES: O=C(NCCCn1cncn1)c1cc(-c2ccsc2)on1] | $^1$H-NMR (DMSO-d$_6$, 500 MHz), ppm (δ): 8.90 (m, 1H), 8.54 (s, 1H), 8.27 (m, 1H), 7.98 (s, 1H), 7.79 (m, 1H), 7.64 (m, 1H), 7.20 (s, 1H), 4.23 (t, 2H), 3.24 (q, 2H), 2.06 (m, 2H) Exact Mass (calc.): 303.08 LC-MS (ESI+) m/e (M + 1)+: 304 |
| 63 | 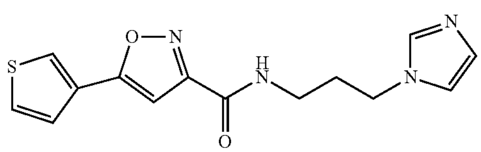 [SMILES: O=C(NCCCn1ccnc1)c1cc(-c2ccsc2)on1] | $^1$H-NMR (CDCl$_3$, 200 MHz), ppm (δ): 7.80 (dd, 1H), 7.54 (s, 1H), 7.38~7.45 (m, 3H), 7.07 (s, 1H), 6.97 (s, 1H), 6.81 (s, 1H), 4.05 (t, 2H), 3.47 (q, 2H), 2.13 (td, 2H) Exact Mass (calc.): 302.08 LC-MS (ESI+) m/e (M + 1)+: 303 |
| 64 | 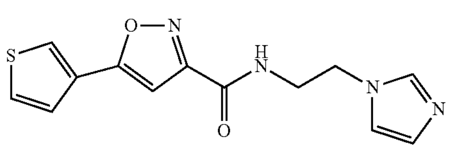 [SMILES: O=C(NCCn1ccnc1)c1cc(-c2ccsc2)on1] | $^1$H-NMR (CDCl$_3$, 200 MHz), ppm (δ): 7.83 (s, 1H), 7.51 (s, 1H), 7.43 (bs, 2H), 7.31 (bs, 1H), 7.09 (s, 1H), 6.97 (s, 1H), 6.81 (s, 1H), 4.23 (t, 2H), 3.79 (q, 2H) Exact Mass (calc.): 288.07 LC-MS (ESI+) m/e (M + 1)+: 289 |
| 65 | 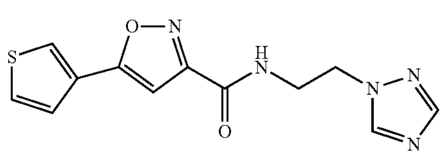 [SMILES: O=C(NCCn1cncn1)c1cc(-c2ccsc2)on1] | $^1$H-NMR (DMSO-d$_6$, 500 MHz), ppm (δ): 8.92 (m, 1H), 8.50 (s, 1H), 8.26 (m, 1H), 7.98 (s, 1H), 7.78 (m, 1H), 7.64 (m, 1H), 7.18 (s, 1H), 4.39 (t, 2H), 3.67 (q, 2H) Exact Mass (calc.): 289.06 LC-MS (ESI+) m/e (M + 1)+: 290 |
| 66 | 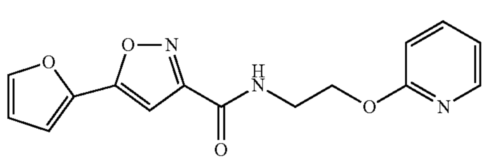 [SMILES: O=C(NCCOc1ccccn1)c1cc(-c2ccco2)on1] | $^1$H-NMR (CDCl$_3$, 500 MHz), ppm (δ): 8.18 (dd, 1H), 7.76 (bs, 1H), 7.59 (t, 1H), 6.89~6.95 (m, 2H), 6.86 (s, 1H), 6.78 (d, 1H), 6.55 (s, 1H), 4.54 (t, 2H), 3.67 (q, 2H) Exact Mass (calc.): 299.09 LC-MS (ESI+) m/e (M + 1)+: 300 |
| 67 | 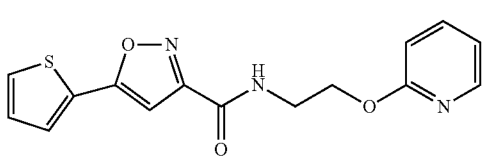 [SMILES: O=C(NCCOc1ccccn1)c1cc(-c2cccs2)on1] | $^1$H-NMR (CDCl$_3$, 500 MHz), ppm (δ): 8.18 (d, 1H), 7.76 (bs, 1H), 7.60 (t, 1H), 7.54 (s, 1H), 7.48 (d, 1H), 7.14 (t, 1H), 6.91 (t, 1H), 6.79 (t, 1H), 4.54 (t, 2H), 3.87 (q, 2H) Exact Mass (calc.): 315.07 LC-MS (ESI+) m/e (M + 1)+: 316 |

TABLE 1-continued

| No. | Chemical Structure | NMR Results |
|---|---|---|
| 68 | 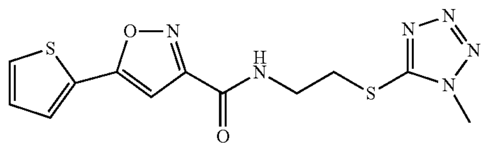 [SMILES: Cn1nnnc1SCCNC(=O)c1cc(-c2cccs2)on1] | $^1$H-NMR (DMSO-$d_6$, 500 MHz), ppm (c.): 315.07 LC-MS (ESI+) m/e (M + 1)+: 316), 7.8 (m, 1H), 7.20 (s, 1H), 3.93 (s, 3H), 3.64 (m, 2H), 3.49 (m, 2H) Exact Mass (calc.): 336.05 LC-MS (ESI+) m/e (M + 1)+: 337 |
| 69 | 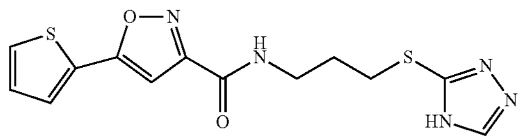 [SMILES: O=C(NCCCSc1nnc[nH]1)c1cc(-c2cccs2)on1] | $^1$H-NMR (DMSO-$d_6$, 500 MHz), ppm (c.): 336.05 LC-MS (ESI+) m/e (M + 1)+: 337), 7.8 (m, 1H), 7.20 (s, 1H), 3 (m, 1H), 7.20 (s, 1H), 3.38 (m, 2H), 3.33 (m, 2H), 1.91 (m, 2H) Exact Mass (calc.): 335.05 LC-MS (ESI+) m/e (M + 1)+: 336 |
| 70 | 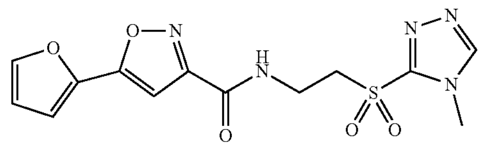 [SMILES: Cn1cnnc1S(=O)(=O)CCNC(=O)c1cc(-c2ccco2)on1] | $^1$H-NMR (DMSO-d6, 500 MHz), ppm (C-MS (ESI+) m/e (M + 1)+: 336), 7.8 (m, 1H), 7.20 (s, 1H), 3 (m, 1H), 7.20 (77 (m, 1H), 3.95 (m, 2H), 3.89 (s, 3H), 3.73 (m, 2H) Exact Mass (calc.): 351.06 LC-MS (ESI+) m/e (M + 1)+: 352 |

The above-mentioned compounds synthesized in the Preparative examples were tested for an effect on the inhibition of restenosis, as follows.

Experimental Example 1

Verification of Active Substance for Wnt/β-Catenin Signal Transduction Using Cell Line (1) Construction of Measurement System for Wnt/β-Catenin Signal Transduction Activity Using Cell Line Two kinds of human cancer cell lines HEK293 and SW480 were used to determine the ex vivo activity of the compounds according to one exemplary embodiment of the present invention. Here, the former represents a cell line whose Wnt signal transduction pathway is intact, and the latter represents a cell line whose Wnt signal transduction pathway is constitutively upregulated (APC gene mutation).

Figure 2:
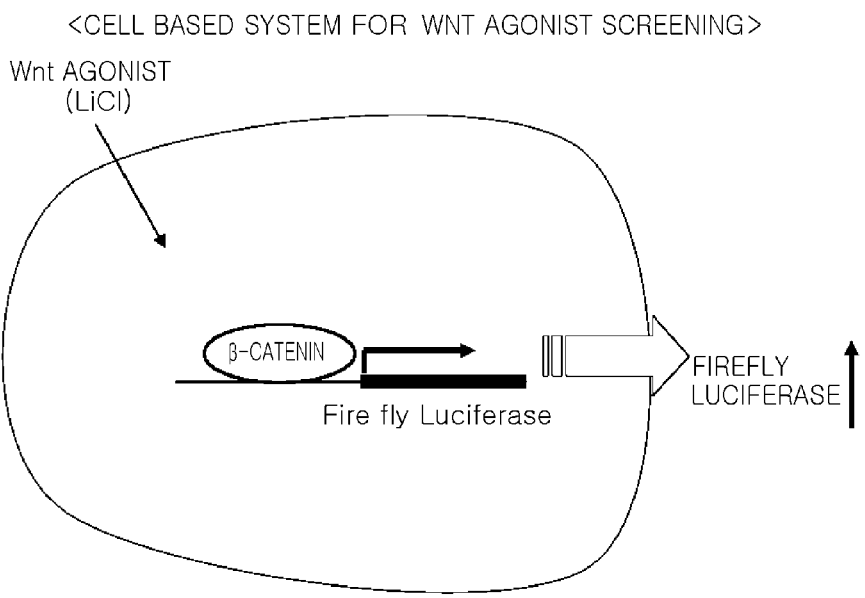
FIG. 2 is a conceptual view illustrating a cell line screening system constructed to evaluate an effect of the isoxazole derivatives on β-catenin activity.

In order to determine the activity of the wnt/β-catenin signal transduction in each cancer cell line, the present inventors introduced a gene as shown in FIG. 1 into cells, the gene having binding sites (5× TCFs) of Tcf/Lef transcription regulation protein to which β-catenin binds and having a firefly fluorescent protein (firefly luciferase) as a marker that can determine the activity of the Tcf/Lef transcription regulation protein. Then, the present inventors constructed a cell based Wnt agonist screening system by treating the gene-introduced cells with G418 to obtain a single clone of a cell line whose Tcf/Lef transcription regulation protein is continuously expressed due to the introduction of the gene. Then, the present inventors performed a cell based screening that indirectly determines the β-catenin activity by measuring an amount of the expressed fluorescent protein using the screening system, as shown in FIG. 2.

Figure 3:
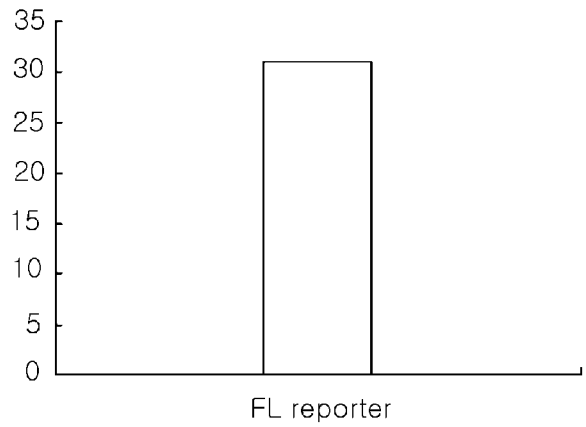
FIG. 3 is a graph illustrating the results in which an action of the screening system as shown in FIG. 2 is determined using lithium chloride that is an agonist of Wnt/β-catenin signal transduction.

When the prepared cell line was treated with lithium chloride (LiCl) that is a positive control in the cell based Wnt agonist screening system as the control for determining the Wnt agonist activity of the isoxazole derivative according to one exemplary embodiment of the present invention, an expression level of the fluorescent protein was measured, and plotted in a graph as shown in FIG. 3.

(2) Measurement of Wnt/β-Catenin Signal Transduction Activity of Isoxazole Derivative The cell line whose cell based Wnt agonist screening system is constructed was incubated in a RPMI 1640 (for SW480) or DMEM (for HEK293) culture medium (containing fetal bovine serum inactivated by the treatment of penicillium-streptomycin (100 Units/mL) and the heat treatment) under a standard culture condition (5% $CO_2$, 37° C., 100% relative humidity (RH)). Then, a single cell suspension was obtained by trypsin treatment and a pipetting method. The single cell suspension was diluted with the same culture medium until the number of the cells was in a range from 8,000 to 15,000 cells per well, and transferred to a 96-well microtiter plate. After the 24-hour incubation, the cells were treated with various concentrations of the isoxazole derivatives prepared in the Preparative example. After the 24-hour incubation, the activityies of the isoxazole derivatives were measured using a luciferase assay kit (Promega, US). The evaluation was carried out according to the method described in the manufacturer's manual, and the activities of the isoxazole derivatives prepared in the Preparative example are listed in the following Table 2 to 3. Lithium chloride (LiCl, 20 mM) that has been known to have an effect agonize the Wnt signal transduction was used as the control, and a relative value to the agoinst effect of the lithium chloride was expressed as percentage.

TABLE 2

Effects on Isoxazole Derivatives on β-Catenin Activities in HEK293 Cell Line

| Original No | Relative Max. Activity (%) | Conc. (μM) |
|---|---|---|
| Control (LiCl) | 100 | 20000 |
| Derivative 1 | 70 | 60 |
| Derivative 2 | 32 | 120 |
| Derivative 3 | 61 | 30 |
| Derivative 4 | 37 | 15 |
| Derivative 5 | 109 | 60 |
| Derivative 6 | 35 | 120 |
| Derivative 7 | 71 | 120 |
| Derivative 8 | 44 | 120 |
| Derivative 17 | <20 | 30 |
| Derivative 21 | <20 | 30 |
| Derivative 22 | 58 | 15 |
| Derivative 23 | 47 | 30 |

TABLE 2-continued

Effects on Isoxazole Derivatives on β-Catenin Activities in HEK293 Cell Line

| Original No | Relative Max. Activity (%) | Conc. (μM) |
|---|---|---|
| Derivative 24 | <20 | 30 |
| Derivative 25 | 42 | 120 |
| Derivative 26 | 48 | 10 |
| Derivative 27 | 58 | 120 |
| Derivative 28 | 869 | 120 |
| Derivative 29 | 67 | 120 |
| Derivative 30 | 1049 | 120 |
| Derivative 31 | 907 | 30 |
| Derivative 32 | <20 | 30 |
| Derivative 33 | <20 | 30 |
| Derivative 34 | <20 | 30 |
| Derivative 35 | 600 | 120 |
| Derivative 36 | 132 | 30 |
| Derivative 37 | 92 | 30 |
| Derivative 38 | 103 | 30 |
| Derivative 39 | 80 | 120 |
| Derivative 40 | 53 | 10 |
| Derivative 41 | 54 | 120 |
| Derivative 42 | 37 | 120 |
| Derivative 43 | 59 | 120 |
| Derivative 44 | 205 | 120 |
| Derivative 45 | 46 | 120 |
| Derivative 46 | 31 | 1 |
| Derivative 47 | 43 | 120 |
| Derivative 48 | 246 | 120 |

TABLE 3

Effects on Isoxazole Derivatives on β-Catenin Activities in SW480 Cell Line

| Compound No. | Relative Max. Activity (%) | Conc. (μM) |
|---|---|---|
| Control l(LiCl) | 100 | 20000 |
| Derivative 1 | 957 | 120 |
| Derivative 2 | 1079 | 120 |
| Derivative 3 | 625 | 60 |
| Derivative 4 | 580 | 120 |
| Derivative 5 | 1696 | 60 |
| Derivative 6 | 130 | 120 |
| Derivative 7 | 283 | 120 |
| Derivative 8 | 296 | 120 |
| Derivative 9 | 551 | 10 |
| Derivative 10 | 344 | 30 |
| Derivative 11 | 896 | 30 |
| Derivative 12 | 676 | 30 |
| Derivative 13 | 1192 | 120 |
| Derivative 14 | 357 | 120 |
| Derivative 15 | 657 | 120 |
| Derivative 16 | 1047 | 30 |
| Derivative 17 | <20 | 30 |
| Derivative 18 | 1016 | 120 |
| Derivative 19 | 1146 | 120 |
| Derivative 20 | 1030 | 30 |
| Derivative 21 | <20 | 30 |
| Derivative 22 | 650 | 600 |
| Derivative 23 | 486 | 60 |
| Derivative 24 | <20 | 30 |
| Derivative 25 | 42 | 120 |
| Derivative 26 | 48 | 10 |
| Derivative 27 | 58 | 120 |
| Derivative 28 | 869 | 120 |
| Derivative 29 | 67 | 120 |
| Derivative 30 | 1049 | 120 |
| Derivative 31 | 907 | 30 |
| Derivative 32 | <20 | 30 |
| Derivative 33 | <20 | 30 |
| Derivative 34 | <20 | 30 |
| Derivative 35 | 600 | 120 |
| Derivative 36 | 132 | 30 |
| Derivative 37 | 92 | 30 |
| Derivative 38 | 103 | 30 |
| Derivative 39 | 80 | 120 |
| Derivative 40 | 53 | 10 |
| Derivative 41 | 54 | 120 |
| Derivative 42 | 37 | 120 |
| Derivative 43 | 59 | 120 |
| Derivative 44 | 205 | 120 |
| Derivative 45 | 46 | 120 |
| Derivative 46 | 31 | 1 |
| Derivative 47 | 43 | 120 |
| Derivative 48 | 246 | 120 |
| Derivative 49 | 1168 | 120 |
| Derivative 50 | 1490 | 120 |
| Derivative 51 | 1136 | 30 |
| Derivative 52 | 1493 | 10 |
| Derivative 53 | 945 | 120 |
| Derivative 54 | 837 | 1 |
| Derivative 55 | 1139 | 30 |
| Derivative 56 | 922 | 30 |
| Derivative 57 | 1091 | 30 |
| Derivative 58 | 93 | 120 |
| Derivative 59 | 374 | 120 |
| Derivative 60 | 304 | 10 |
| Derivative 61 | 113 | 120 |
| Derivative 62 | 1060 | 30 |
| Derivative 63 | 1287 | 120 |
| Derivative 64 | 871 | 30 |
| Derivative 65 | 414 | 120 |
| Derivative 66 | 1086 | 10 |
| Derivative 67 | 1753 | 120 |

Experimental Example 2

Verification of Ex vivo Wnt/β-Catenin Signal Transduction Activity of Isoxazole Derivatives by Measurement of Amount of Accumulated β-Catenin An HEK293 cell line was incubated in a DMEM culture medium (containing fetal bovine serum inactivated by the treatment of penicillium-streptomycin (100 Units/mL) and the heat treatment) under a standard culture condition (5% $CO_2$, 37° C., 100% RH). A test compound was dissolved in dimethylsulfoxide (DMSO), and finally used at a concentration of 30 or 60 μM. The HEK293 cells ($3 \times 10^7$) were incubated for 24 hours in a test compound-containing culture medium and a test compound-free culture medium, respectively. In order to selectively isolate only cytoplasm from the HEK293 cells, the HEK293 cells was lysed by treating the HEK293 cells with a high-concentration salt solution, centrifuging the obtained cell suspension at a rotary speed of 200 g (rpm) for 10 minutes. Then, a pellet of cell nucleus and membrane was removed and a supernatant was recovered.

Figure 4:
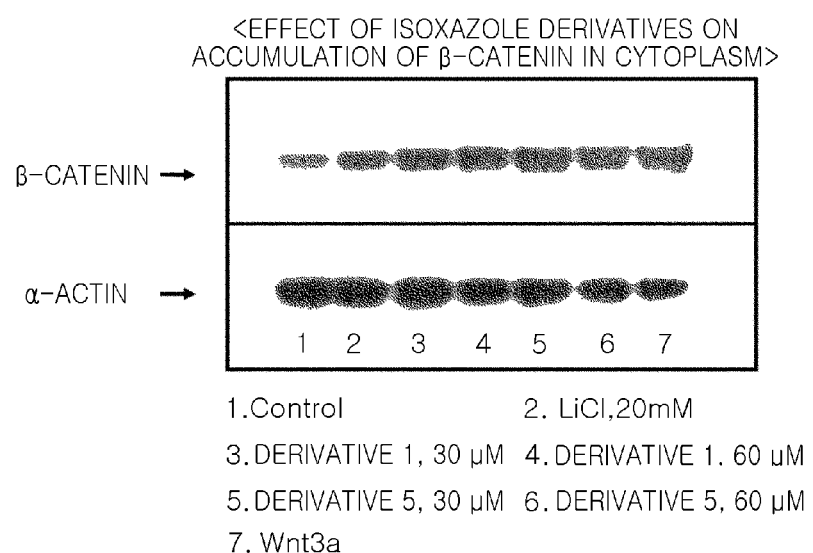
FIG. 4 is a diagram illustrating the results in which an amount of accumulated β-catenin in cell is determined through a western blot experiment using a human β-catenin antibody when HEK293 cell is treated with various concentrations of an isoxazole derivative.

The obtained cytoplasm solution was electrophoresized in a 10% PAGE gel, and then probed with β-catenin antibody (Upstate Biotechnology Inc.). The probing was carried out using a chemiluminescence system (ECL, Amersham). Actin protein was used as the control to compare an equivalent amount of the protein. The results are shown in FIG. 4. As shown in FIG. 4, it was confirmed from the western blotting assay that, when the cells were treated with the compounds, β-catenin was accumulated in the cell, depending on the concentration of the compounds.

Experimental Example 3

Ex vivo Test of Endothelial Eell Proliferation and Smooth Muscle Cell Proliferation on Isoxazole Derivatives (1) Test of Endothelial Cell Proliferation An HUVEC (human umbrical vein endothelial cell, Cambrex, US) cell line at 3-10 passages was incubated in an EGM2 (endothelial growth medium, Cambrex, US) culture medium under a standard culture condition ($O_2$ 95%, 5% $CO_2$, 37° C., 100% RH). $1\times10^4$ Cells was divided into a 24-well plate, and cultured for a day so that the cells can be fixed into the 24-well plate. In order to allow the cells to enter interphase, the cells were washed three times with PBS, and the EGM2 culture medium was replaced by EBM2 (endothelial basal medium, Cambrex) including 1% fetal bovine serum and 1% antibiotic-antimycotic (Gibco, US), and the cells were incubated for a day. After the used medium was removed, an EBM2 including 1% fetal bovine serum and 1% antibiotic-antimycotic (Gibco) solution supplemented with a drug was added to the cells, and the cell solution was then cultured for two days. After the cell culture, morphology of the cells was observed under a microscope. Then, the cells were detached from the plate using trypsin, and counted using a hemacytometer. 0.1% DMSO dissolved in saline was used as the vehicle control.

(2) Test of Vascular Smooth Muscle Cell Proliferation

An SMC (rat aortic smooth muscle cell) cell line at 3-10 passages was incubated in a culture medium of SmGM (Smooth muscle cell growth medium, Cambrex) including 5% fetal bovine serum and 1% antibiotic antimycotic reagent (Gibco, US) under a standard culture condition (95% $O_2$, 5% $CO_2$, 37° C., 100% RH). $2\times10^4$ Cells were divided into a 24-well plate, and cultured for a day so that the cells can be fixed into the 24-well plate. The cells were washed three times with PBS, put into a solution of SmGM including 5% fetal bovine serum and 1% antibiotic-antimycotic (Gibco), and then incubated for a day. After the used medium was removed, an SmGM including 5% fetal bovine serum solution supplemented with a corresponding drug was added to the cells, and the cell solution was then cultured for two days. After the cell culture, morphology of the cells was observed under a microscope. Then, the cells were detached from the plate using trypsin, and counted using a hemacytometer. 0.1% DMSO dissolved in saline was used as the vehicle control.

(3) Results

Figure 5:
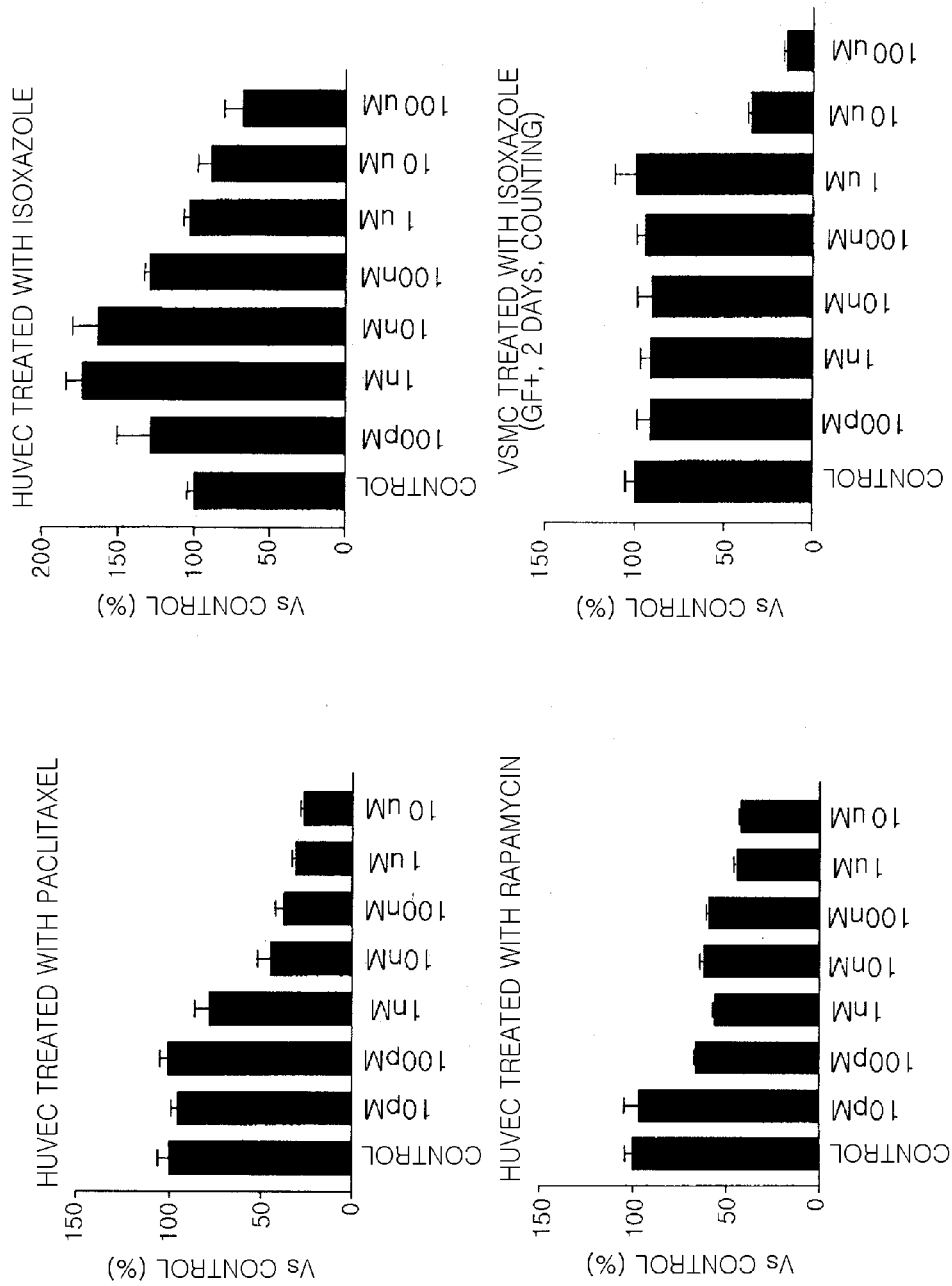
FIG. 5 is a graph illustrating an effect of the isoxazole derivative according to one exemplary embodiment of the present invention and the conventional restenosis inhibitors, paclitaxel and rapamycin, on the endothelial cell proliferation and the smooth muscle cell proliferation.
Figure 6:
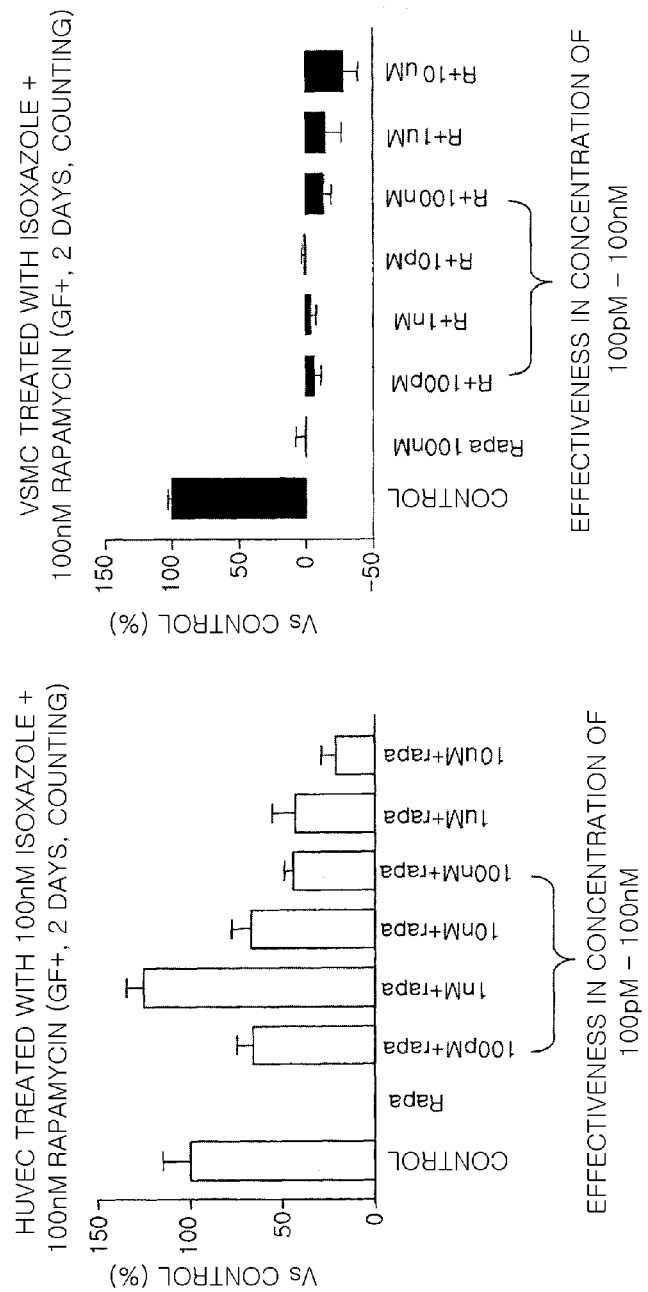
FIG. 6 is a graph illustrating an effect on the endothelial cell proliferation and the vascular smooth muscle cell proliferation when each cell is treated with the isoxazole derivative and the rapamycin together.
Figure 7:
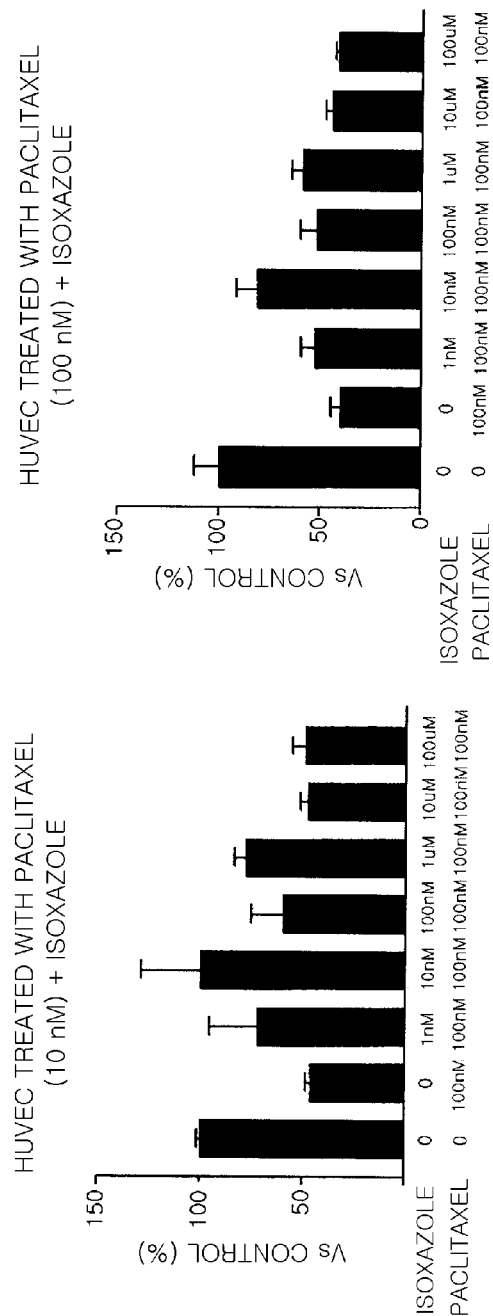
FIG. 7 is a graph illustrating an effect on the endothelial cell proliferation when each cell is treated with the isoxazole derivative and the paclitaxel together.

The test results are shown in FIGS. 5 to 10, respectively. As shown in FIG. 5, it was revealed that the conventional anti-stenosis agents, paclitaxel and rapamycin, inhibit the proliferation of HUVEC when the cells are treated with an increasing concentration of the anti-stenosis agents, but the derivative 5 according to one exemplary embodiment of the present invention increases or maintains the proliferation of HUVEC. Also, it was observed that, as a concentration of the derivative 5 according to one exemplary embodiment of the present invention increases, the cell number of vascular smooth muscle cells (VSMC) in a culture medium of SmGM (Smooth muscle cell growth medium, Cambrex) including 5% fetal bovine serum and 1% antibiotic antimycotic reagent (Gibco, US) under a standard culture condition (95% $O_2$, 5% $CO_2$, 37° C., 100% RH) is reduced. Also, as shown in FIG. 6, it was revealed that the proliferation of the endothelial cells is recovered when the compound is used together with the conventional drug 'rapamycin', while the proliferation of the endothelial cells is inhibited when the endothelial cells are treated with only the rapamycin. Also, it was observed that the proliferation of the vascular smooth muscle cells is inhibited more significantly when the rapamycin is used together with the compound than when the rapamycin is used alone. Similarly, it was observed that the proliferation of the endothelial cells is recovered when the conventional drug 'paclitaxel' is used together with the compound, while the proliferation of the endothelial cells is inhibited when the paclitaxel is used alone, as shown in FIG. 7.

Figure 8:
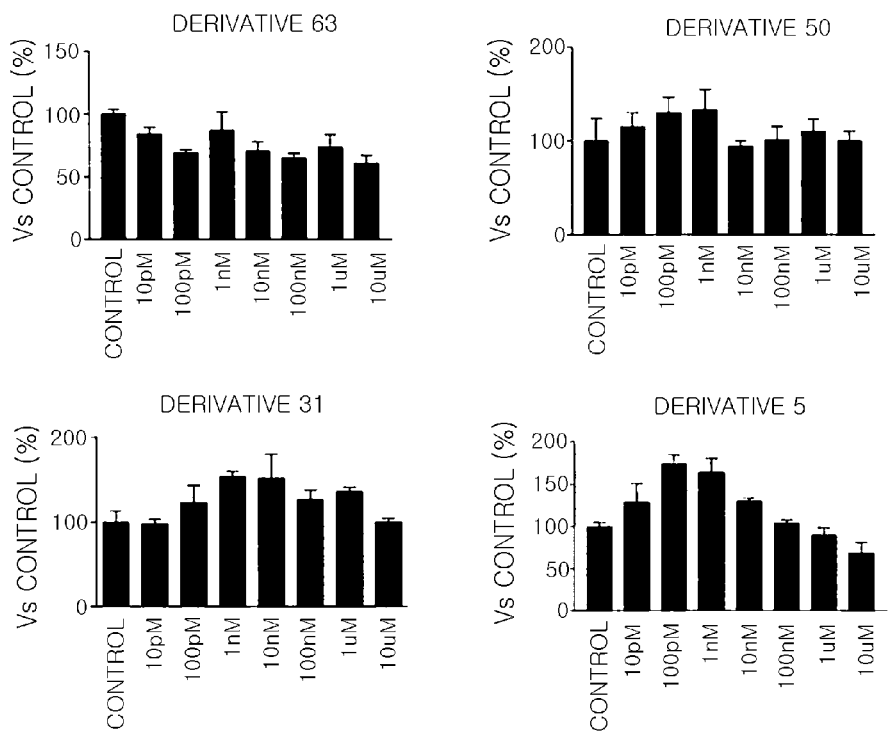
FIG. 8 is a graph illustrating an effect of various isoxazole derivatives according to one exemplary embodiment of the present invention on the endothelial cell proliferation.
Figure 9:
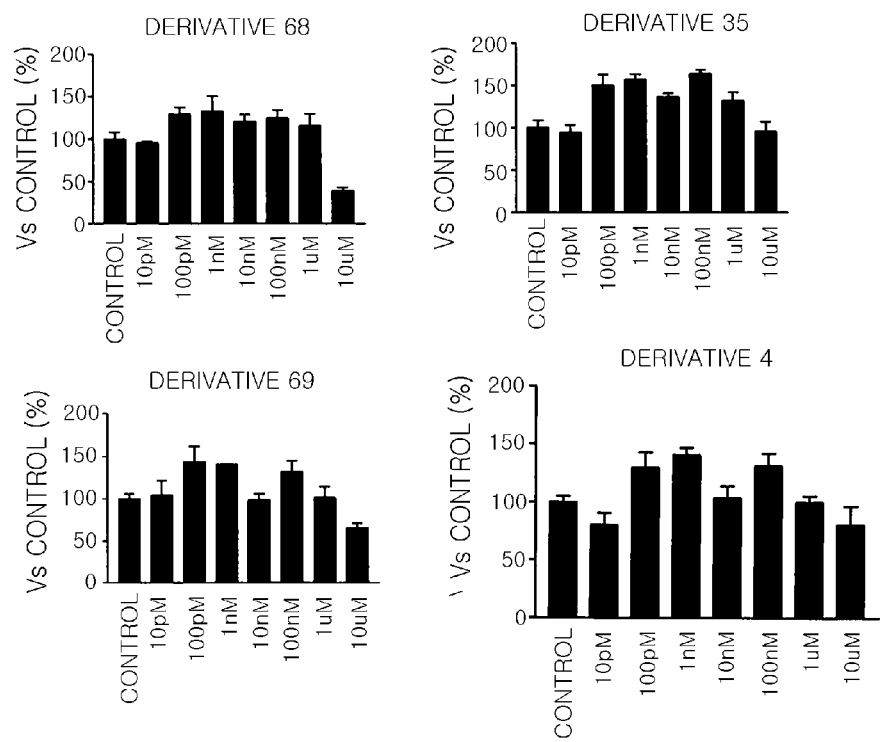
FIG. 9 is a graph illustrating an effect of various isoxazole derivatives according to one exemplary embodiment of the present invention on the endothelial cell proliferation.
Figure 10:
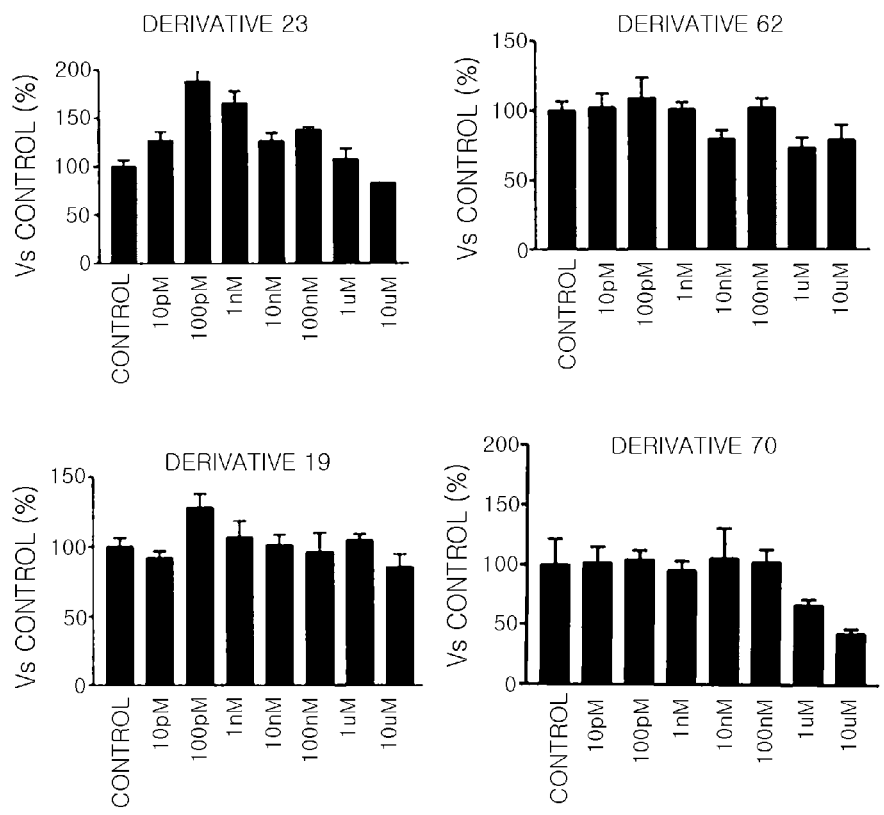
FIG. 10 is a graph illustrating an effect of various isoxazole derivatives according to one exemplary embodiment of the present invention on the endothelial cell proliferation.

In addition to the derivative 5, the effects of the derivatives 4, 19, 23, 31, 35, 50, 62, 63, 68, 69 and 70 on the proliferation of the endothelial cells were also measured. As a result, it was revealed that the compounds inhibit or maintain the proliferation of the endothelial cells as shown in FIGS. 8 to 10. Therefore, it was revealed that the compounds used in the present invention are drugs that are effective to prevent and treat the restenosis since the compounds inhibit the proliferation of the smooth muscle cells and enhance the proliferation of the endothelial cells.

Experimental example 4

Effect of Isoxazole Derivative on Restenosis Inhibition in Rat Carotid Artery Injury Model The effects of the isoxazole derivatives on the restenosis inhibition were measured using a rat carotid artery injury model.

Figure 11:
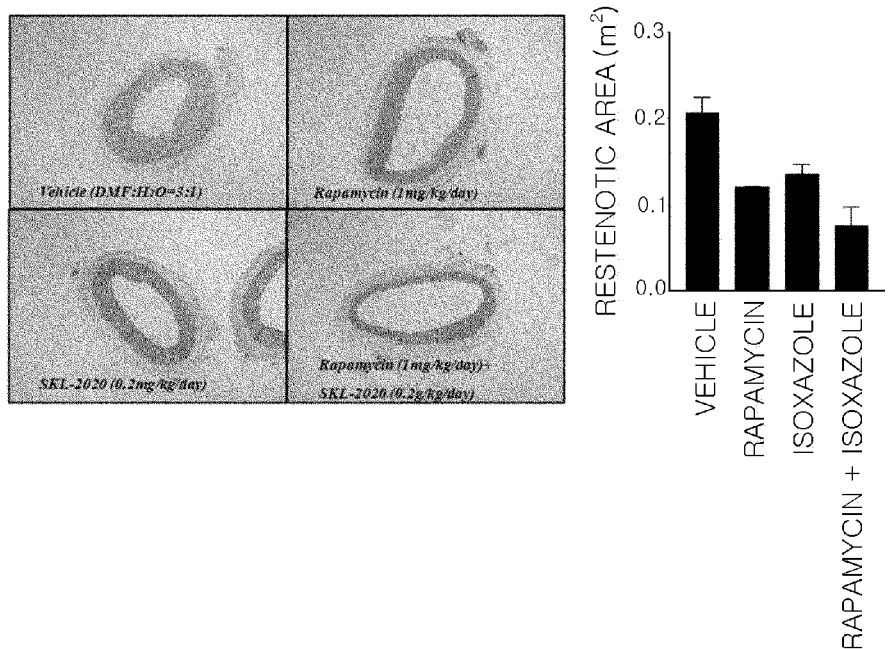
FIG. 11 is a diagram illustrating an effect on the inhibition of restenosis when each cell is treated with the isoxazole derivative and the rapamycin together by using a rat carotid artery injury model.
Figure 13:
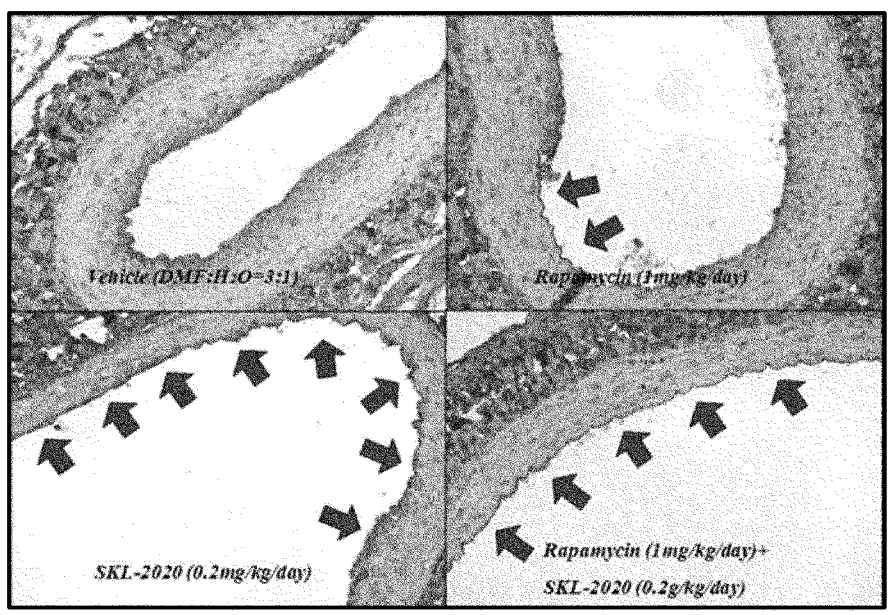
FIG. 13 is a diagram illustrating an effect on the re-endothelization when each cell is treated with the isoxazole derivative and the rapamycin together by using a rat carotid artery injury model.

White rats weighed 350 to 400 g were anesthetized with ketamine and xylene, and their surgery regions were shaved and sterilized with betadine. Skin on the neck region was cut by about 2 cm, and a rat carotid artery was found using a mosquito. A blood flow was prevented by hanging a thread on the carotid artery and an internal carotid artery, followed by tying an external carotid artery with a thread. A 2F forgarty catheter (Baxter, US) was inserted into a blood vessel between the external carotid artery and the carotid artery to wound a carotid artery region three times. Then, the wounded carotid artery region was tied with a thread to allow a blood flow through the carotid artery and the internal carotid artery and prevent hemorrhage between the carotid artery and the external carotid artery, and the surgery region was closed with stitches. Each of rear neck skins were cut by approximately 1 cm, and an osmotic pump containing a drug is inserted into the blood vessel and closed with stitches. After 1 week to observe the endothelial cells and 2 weeks to observe the restenosis, all blood was extracted from each subject rat using a perfusion, carotid arteries were taken from the rats and their tissue slides were made to observe their section of blood vessel. The derivative 5(SKL-2020) was used as the experimental group, and 75% DMF (dimethylformamide) (DMF:$H_2O$=3:1) was used as the vehicle control. The experimental results are shown in FIG. 11. As shown in FIG. 11 and FIG. 13, it was revealed that a restenotic area of the blood vessel is more significantly reduced in size when 200 μg/kg/day of the derivative 5 was administered for two weeks than when the derivative 5 was not administered. Also, it is considered that, since the compound has a more significant restenosis inhibition effect when cells were treated with the compound together with rapamycin than when the cells were treated with only the compound, the compound according to one exemplary embodiment of the present invention has a synergic effect when the compound is used together with the conventional restenosis inhibitor.

Experimental Example 5

Figure 12:
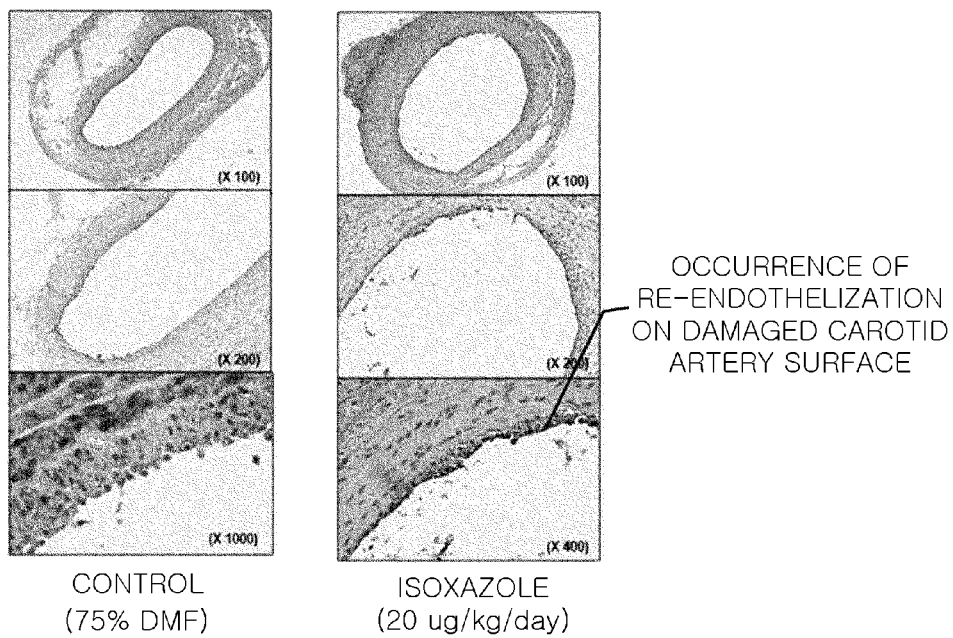
FIG. 12 is a diagram illustrating an effect of the isoxazole derivative according to one exemplary embodiment of the present invention on the re-endothelization by using a rat carotid artery injury model.

Observation of Re-Endothelization by Isoxazole Derivative in Rat Carotid Artery Injury Model In order to observe a re-endothelization level by a drug, a tissue section slide of blood vessel was treated with 0.1% hydrogen peroxidase to remove endogenous peroxidase, and reacted at 4° C. with vWF (von willebrand factor, DakoCytomation, US) Ab that stains endothelial cells of mice. Then, the tissue section was treated with biotinylated anti-rat IgG (Jackson Immuno Research Laboratories, US) and stained using an avidin-biotin complex (ABC)-peroxidase kit elite kit; Vector Laboratories). The tissue section slide was observed and photographed under a microscope. The derivative 5 was used as the experimental group, and 75% DMF (dimethylformamide) (DMF:$H_2O$=3:1) was used as the vehicle control. The experimental results are shown in FIG. 12 and FIG. 13. As shown in FIG. 12, it was revealed that the re-endothelization on a damaged carotid artery surface occurs more significantly when 200 μg/kg/day of the derivative 5 was administered for two weeks than when the derivative 5 was not administered. As shown in FIG. 13, it is also considered that, since the re-endothelization is more significantly increased when cells were treated with the compound together with rapamycin than when the cells were treated with only the compound, the compound according to one exemplary embodiment of the present invention has a synergic effect when the compound is used together with the conventional restenosis inhibitor.

Experimental Example 6

Effect of Isoxazole Derivative on Restenosis Inhibition in Pig Coronary Stent Model An effect of the isoxazole derivative on restenosis inhibition was determined using a pig coronary stent model.

All pigs receiving a surgical operation were treated with an antithrombotic agent 'clopidogrel' (35 mg/day) and aspirin (100 mg/day) before one week of the surgical operation. Pigs weighed 30 to 40 kg were anesthetized with ketamine (20 mg/kg IM) and xylazine (2 mg/kg IM), and their aesthesia was maintained by connecting an infusion set to their ear veins and allowing a ketamine/xylazine solution (ketamin 50 g+xylazine 10 g/500 ml saline) to flow in the ear veins according to the aesthesia state. Pig surgery regions were shaved, sterilized with betadine. Skin on the neck was cut by approximately 5 cm, and a pig carotid artery was found using a mosquito, and 1 ml of heparin (5,000 IU) was administered to pigs. Angiocardiography was performed using a SIREMOBIL 245B angiocardiographer (commercially available from Siemens). A stent (diameter: 3.0 mm; length: 15 mm) was used for surgical operation on LAD, RAD and RCX by expanding the stent at a ratio 1.3:1 of stent:vein diameter, and a position of stent transplantation was previously determined using the imaging system.

After 28 days, pigs were intravenously injected with KCl (40 meq/l) under a conventional aesthesia condition to induce pig cardioplegia, and hearts were extracted pigs. Right after the extraction of pig hearts, the pig heart blood vessels were perfused with 500 ml of physiological saline obtained by diluting 1 ml of heparin (5000 IU), and fixed in 500 ml of 10% formalin solution through the perfusion. Then, the entire pig hearts were fixed by dipping them into a 10% formalin solution buffered with physiological saline. Stent-engrafted LAD, RAD and RCX blood vessel regions were extracted, fixed in a 10% formalin solution for a day, dehydrated with ethanol, and then embedded with methyl methacrylate for one month. After the embedding, the pig blood vessels were cut by 10 um in length using a laser cutter, grated into a size of 5 to 7 um using a sandpaper, and then observed under an optical microscope to determine the presence of restenosis. In this experiment, a stent that does not contain a drug and is coated with PLGA polymer was used as the negative control, and a stent containing rapamycin in addition to the PLGA polymer was used as to the positive control. A stent containing a mixture of 180 μg of rapamycin with an increasing amount (45 μg, 90 μg and 180 μg) of the derivative 5 was used as the experimental group.

Figure 14:
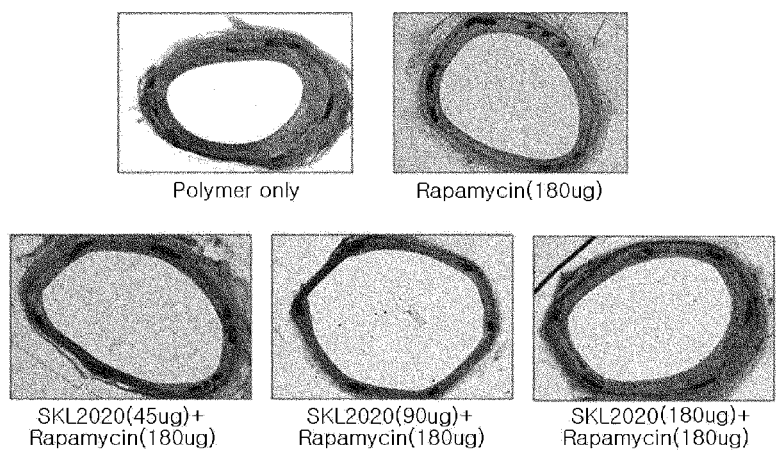
FIG. 14 is a diagram illustrating an effect of the isoxazole derivative according to one exemplary embodiment of the present invention on the inhibition of restenosis by using a pig coronary stent model.
Figure 14:
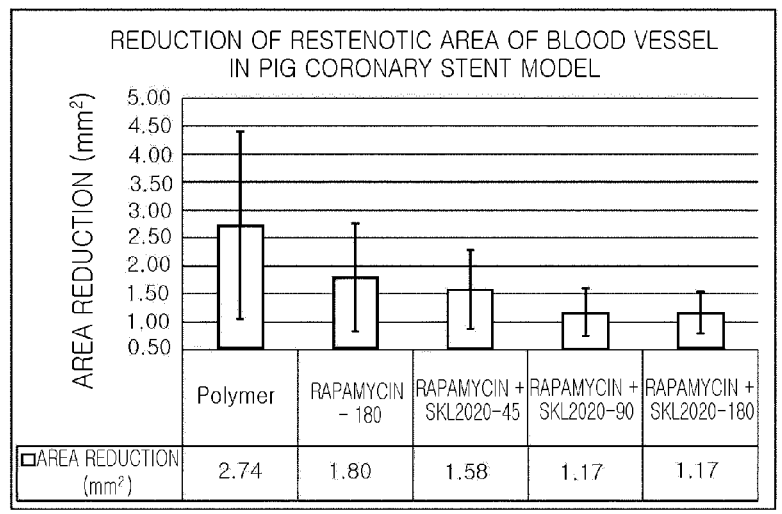

The experiment results are shown in FIG. 14. As shown in FIG. 14, it was revealed that restenotic areas of blood vessels are significantly reduced from 2.74 $mm^2$ to 1.80 $mm^2$ in the rapamycin-treated groups, compared to the negative control, and it was also confirmed that a lumen losses of blood vessel are further reduced in the derivative 5-treated groups, compared to the rapamycin-treated group.

Experimental Example 7

Observation of Re-Endothelization by Isoxazole Derivatives in Pig Coronary Stent Model In order to observe a re-endothelization level by a drug, a tissue section slide of pig blood vessel was reacted at 4° C. with vWF (von willebrand factor, DakoCytomation, US) Ab that stains endothelial cells of mice. Then, the tissue section was treated with biotinylated anti-human IgG (Jackson Immuno Research Laboratories, US) and stained using an avidin-biotin complex (ABC)-peroxidase kit. The tissue section slide was observed and photographed under a fluorescence microscope. The experimental results are shown in FIG. 15.

Figure 15:
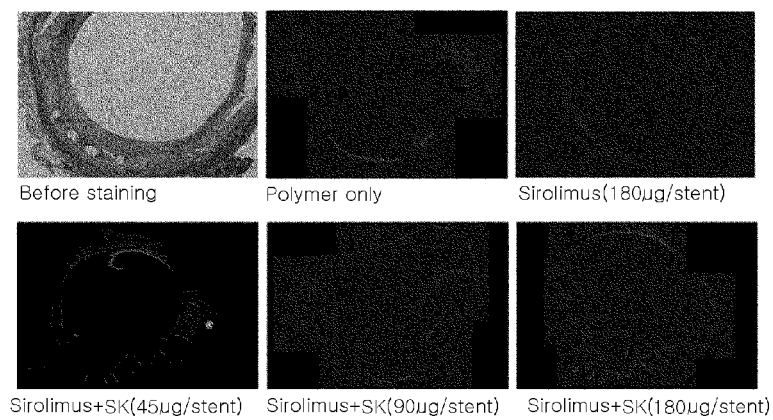
FIG. 15 is a diagram illustrating an effect of the isoxazole derivative according to one exemplary embodiment of the present invention on the re-endothelization by using a pig coronary stent model.
Figure 15:
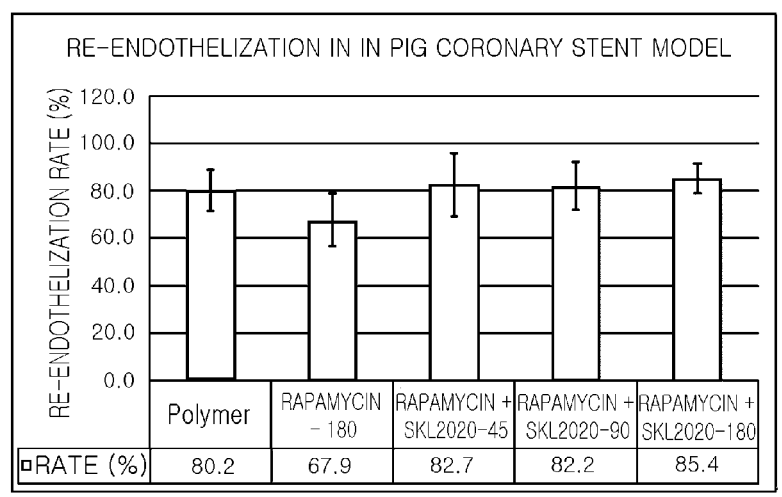

As shown in FIG. 15, it was revealed that, when the stent is coated with the polymer, a re-endothelization rate (healing %) was 80.2%, but the re-endothelization rate (healing %) is reduced to 67.9% by the rapamycin. It was confirmed that, 4 weeks after the derivative 5 was administered to pigs, the re-endothelization on the damaged carotid artery surface was significantly recovered to such a level that the cells are treated with the rapamycin. It is considered that, when the compound according to one exempelary embodiment of the present invention is used together with the conventional restenosis inhibitor, the compound functions to prevent late stent thrombosis by inhibiting the reduction of re-endothelization that is caused by the side effects.

What is claimed is:
1. A method for reducing or delaying the onset of a clinical marker or symptom of restenosis or treating restenosis comprising:
administering to a subject in need thereof a pharmaceutical composition which comprises a therapeutically effective amount of a compound of Formula 1, or a pharmaceutically acceptable salt thereof:

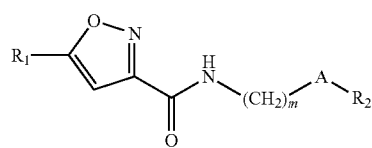

Formula 1 wherein,
$R_1$ is furanyl or thienyl, wherein $R_1$ is optionally substituted with one or more substituents independently selected from the group consisting of acyl, amino, carboalkoxy, carboxy, carboxyamino, —O—(C=O)—$NH_2$, cyano, halo, hydroxy, nitro, alkyl, cycloalkyl, aryl, alkoxy, aryloxy, sulfoxy and guanido, m is 2 or 3, A is a bond, —O—, —S—, —SO— or —SO$_2$—, and R$_2$ is imidazolyl, pyrazolyl, triazolyl, tetrazolyl or pyridinyl, wherein R$_2$ is optionally substituted with one or more substituents independently selected from the group consisting of acyl, amino, carboalkoxy, carboxy, carboxyamino, —O—(C=O)—NH$_2$, cyano, halo, hydroxy, nitro, alkyl, cycloalkyl, aryl, alkoxy, aryloxy, sulfoxy and guanido.

2. A method for reducing or delaying the onset of a clinical marker or symptom of restenosis or treating restenosis comprising:

administering to a subject in need thereof a pharmaceutical composition which comprises a therapeutically effective amount of a compound selected from the group consisting of the following compounds or a pharmaceutical acceptable salt thereof:

5-furan-2-yl-isoxazole-3-carboxylic acid(3-imidazol-1-yl-propyl)-amide,
5-furan-2-yl-isoxazole-3-carboxylic acid(2-pyridin-2-yl-ethyl)-amide,
5-furan-2-yl-isoxazole-3-carboxylic acid(2-pyridin-3-yl-ethyl)-amide,
5-furan-2-yl-isoxazole-3-carboxylic acid(2-imidazol-1-yl-ethyl)-amide,
5-furan-2-yl-isoxazole-3-carboxylic acid(2-pyridin-4-yl-ethyl)-amide,
5-furan-2-yl-isoxazole-3-carboxylic acid[2-(2-methyl-imidazol-1-yl)-ethyl]-amide,
5-furan-2-yl-isoxazole-3-carboxylic acid[2-(5-methyl-imidazol-1-yl)-ethyl]-amide,
5-furan-2-yl-isoxazole-3-carboxylic acid[2-(4-methyl-imidazol-1-yl)-ethyl]-amide,
5-furan-2-yl-isoxazole-3-carboxylic acid(2-[1,2,4]triazol-1-yl-ethyl)-amide,
5-furan-2-yl-isoxazole-3-carboxylic acid(2-pyrazol-1-yl-ethyl)-amide,
5-furan-2-yl-isoxazole-3-carboxylic acid(2-[1,2,3]triazol-1-yl-ethyl)-amide,
5-furan-2-yl-isoxazole-3-carboxylic acid(2-[1,2,3]triazol-2-yl-ethyl)-amide,
5-furan-2-yl-isoxazole-3-carboxylic acid(2-tetrazol-2-yl-ethyl)-amide,
5-furan-2-yl-isoxazole-3-carboxylic acid(2-tetrazol-1-yl-ethyl)-amide,
5-furan-2-yl-isoxazole-3-carboxylic acid[3-(2-methyl-imidazol-1-yl)-propyl]-amide,
5-furan-2-yl-isoxazole-3-carboxylic acid(3-pyrazol-1-yl-propyl)-amide,
5-furan-2-yl-isoxazole-3-carboxylic acid(3-[1,2,3]triazol-1-yl-propyl)-amide,
5-furan-2-yl-isoxazole-3-carboxylic acid(3-[1,2,3]triazol-2-yl-propyl)-amide,
5-furan-2-yl-isoxazole-3-carboxylic acid(3-[1,2,4]triazol-1-yl-propyl)-amide,
5-furan-2-yl-isoxazole-3-carboxylic acid(3-tetrazol-1-yl-propyl)-amide,
5-furan-2-yl-isoxazole-3-carboxylic acid(3-tetrazol-2-yl-propyl)-amide,
5-furan-2-yl-isoxazole-3-carboxylic acid[3-(4-methyl-imidazol-1-yl)-propyl]-amide,
5-thiophen-2-yl-isoxazole-3-carboxylic acid(3-imidazol-1-yl-propyl)-amide,
5-thiophen-2-yl-isoxazole-3-carboxylic acid(3-[1,2,4]triazol-1-yl-propyl)-amide,
5-thiophen-2-yl-isoxazole-3-carboxylic acid(2-imidazol-1-yl-ethyl)-amide,
5-thiophen-2-yl-isoxazole-3-carboxylic acid(2-pyrazol-1-yl-ethyl)-amide,
5-thiophen-2-yl-isoxazole-3-carboxylic acid(2-[1,2,4]triazol-1-yl-ethyl)-amide,
5-thiophen-2-yl-isoxazole-3-carboxylic acid(2-[1,2,3]triazol-2-yl-ethyl)-amide,
5-thiophen-2-yl-isoxazole-3-carboxylic acid(2-[1,2,3]triazol-1-yl-ethyl)-amide,
5-thiophen-2-yl-isoxazole-3-carboxylic acid(2-pyridin-3-yl-ethyl)-amide,
5-thiophen-2-yl-isoxazole-3-carboxylic acid(2-pyridin-4-yl-ethyl)-amide,
5-(5-bromo-thiophen-2-yl)-isoxazole-3-carboxylic acid (3-imidazol-1-yl-propyl)-amide,
5-furan-3-yl-isoxazole-3-carboxylic acid(3-imidazol-1-yl-propyl)-amide,
5-furan-3-yl-isoxazole-3-carboxylic acid(3-[1,2,4]-triazol-1-yl-propyl)-amide,
5-furan-3-yl-isoxazole-3-carboxylic acid(2-[1,2,4]-triazol-1-yl-ethyl)-amide,
5-thiophen-3-yl-isoxazole-3-carboxylic acid(3-[1,2,4]-triazol-1-yl-propyl)-amide,
5-thiophen-3-yl-isoxazole-3-carboxylic acid(3-imidazol-1-yl-propyl)-amide,
5-thiophen-3-yl-isoxazole-3-carboxylic acid(2-imidazol-1-yl-ethyl)-amide,
5-thiophen-3-yl-isoxazole-3-carboxylic acid(2-[1,2,4]-triazol-1-yl-ethyl)-amide,
5-furan-2-yl-isoxazole-3-carboxylic acid[2-(pyridin-2-yl-oxy)-ethyl]-amide,
5-thiophen-2-yl-isoxazole-3-carboxylic acid[2-(pyridin-2-yl-oxy)-ethyl]-amide,
5-thiophen-2-yl-isoxazole-3-carboxylic acid[2-(1-methyl-1H-tetrazol-5-yl-sulfanyl)-ethyl]-amide,
5-thiophen-2-yl-isoxazole-3-carboxylic acid[3-(4H-[1,2,4]triazol-3-yl-sulfanyl)-propyl]-amide, and
5-furan-2-yl-isoxazole-3-carboxylic acid[2-(4-methyl-4H-[1,2,4]triazol-3-sulfonyl)-ethyl]-amide.

3. The method of claim 1, wherein the pharmaceutical composition further comprises rapamycin or paclitaxel.

4. The method of claim 1, wherein the restenosis is selected from the group consisting of coronary restenosis after percutaneous transluminal coronary angioplasty (PTCA), restenosis after percutaneous intervention for cerebral and peripheral vascular diseases, vascular stenosis after various vascular surgeries, vascular stenosis after bypass operation and arteriovenous fistula angioplasty, stenosis after self-blood vessel and artificial blood vessel transplantation, and arteriosclerosis.

5. The method of claim 1, wherein the pharmaceutical composition further comprises a pharmaceutically acceptable carrier.

6. The method of claim 1, wherein the pharmaceutical composition is parenterally administered in the form of a stent coating agent.

7. The method of claim 2, wherein the pharmaceutical composition further comprises rapamycin or paclitaxel.

8. The method of claim 2, wherein the restenosis is selected from the group consisting of coronary restenosis after percutaneous transluminal coronary angioplasty (PTCA), restenosis after percutaneous intervention for cerebral and peripheral vascular diseases, vascular stenosis after various vascular surgeries, vascular stenosis after bypass operation and arteriovenous fistula angioplasty, stenosis after self-blood vessel and artificial blood vessel transplantation, and arteriosclerosis.

9. The method of claim 2, wherein the pharmaceutical composition further comprises a pharmaceutically acceptable carrier.

10. The method of claim 2, wherein the pharmaceutical composition is parenterally administered in the form of a stent coating agent.

11. The method of claim 1, wherein $R_1$ is furanyl or thienyl.

12. The method of claim 1, wherein $R_2$ is imidazolyl, triazolyl, tetrazolyl or pyridinyl.

13. The method of claim 1, wherein the method is for treating restenosis and the compound is 5-furan-2-yl-isoxazole-3-carboxylic acid (2-pyridin-4-yl-ethyl)-amide.

14. The method of claim 2, wherein the pharmaceutical formulation is administered in the form of an oral formulation, a parenteral formulation, an injectable formulation or a transcutaneous formulation.

15. The method of claim 2, wherein the pharmaceutical formulation is administered topically.

16. The method of claim 2, wherein the compound is selected from:
   5-furan-2-yl-isoxazole-3-carboxylic acid(3-imidazol-1-yl-propyl)-amide,
   5-furan-2-yl-isoxazole-3-carboxylic acid(2-pyridin-2-yl-ethyl)-amide,
   5-furan-2-yl-isoxazole-3-carboxylic acid(2-pyridin-3-yl-ethyl)-amide,
   5-furan-2-yl-isoxazole-3-carboxylic acid(2-imidazol-1-yl-ethyl)-amide,
   5-furan-2-yl-isoxazole-3-carboxylic acid(2-pyridin-4-yl-ethyl)-amide,
   5-furan-2-yl-isoxazole-3-carboxylic acid[2-(2-methyl-imidazol-1-yl)-ethyl]-amide,
   5-furan-2-yl-isoxazole-3-carboxylic acid[2-(5-methyl-imidazol-1-yl)-ethyl]-amide,
   5-furan-2-yl-isoxazole-3-carboxylic acid[2-(4-methyl-imidazol-1-yl)-ethyl]-amide,
   5-furan-2-yl-isoxazole-3-carboxylic acid(2-[1,2,4]triazol-1-yl-ethyl)-amide,
   5-furan-2-yl-isoxazole-3-carboxylic acid(2-pyrazol-1-yl-ethyl)-amide,
   5-furan-2-yl-isoxazole-3-carboxylic acid(2-[1,2,3]triazol-1-yl-ethyl)-amide,
   5-furan-2-yl-isoxazole-3-carboxylic acid(2-[1,2,3]triazol-2-yl-ethyl)-amide,
   5-furan-2-yl-isoxazole-3-carboxylic acid(2-tetrazol-2-yl-ethyl)-amide,
   5-furan-2-yl-isoxazole-3-carboxylic acid(2-tetrazol-1-yl-ethyl)-amide,
   5-furan-2-yl-isoxazole-3-carboxylic acid[3-(2-methyl-imidazol-1-yl)-propyl]-amide,
   5-furan-2-yl-isoxazole-3-carboxylic acid(3-pyrazol-1-yl-propyl)-amide,
   5-furan-2-yl-isoxazole-3-carboxylic acid(3-[1,2,3]triazol-1-yl-propyl)-amide,
   5-furan-2-yl-isoxazole-3-carboxylic acid(3-[1,2,3]triazol-2-yl-propyl)-amide,
   5-furan-2-yl-isoxazole-3-carboxylic acid(3-[1,2,4]triazol-1-yl-propyl)-amide,
   5-furan-2-yl-isoxazole-3-carboxylic acid(3-tetrazol-1-yl-propyl)-amide,
   5-furan-2-yl-isoxazole-3-carboxylic acid(3-tetrazol-2-yl-propyl)-amide,
   5-furan-2-yl-isoxazole-3-carboxylic acid[3-(4-methyl-imidazol-1-yl)-propyl]-amide,
   5-furan-3-yl-isoxazole-3-carboxylic acid(3-imidazol-1-yl-propyl)-amide,
   5-furan-3-yl-isoxazole-3-carboxylic acid(3-[1,2,4]-triazol-1-yl-propyl)-amide,
   5-furan-3-yl-isoxazole-3-carboxylic acid(2-[1,2,4]-triazol-1-yl-ethyl)-amide,
   5-furan-2-yl-isoxazole-3-carboxylic acid[2-(pyridin-2-yl-oxy)-ethyl]-amide, and
   5-furan-2-yl-isoxazole-3-carboxylic acid[2-(4-methyl-4H-[1,2,4]triazol-3-sulfonyl)-ethyl]-amide.

17. The method of claim 2, wherein the compound is selected from:
   5-thiophen-2-yl-isoxazole-3-carboxylic acid(3-imidazol-1-yl-propyl)-amide,
   5-thiophen-2-yl-isoxazole-3-carboxylic acid(3-[1,2,4]-triazol-1-yl-propyl)-amide,
   5-thiophen-2-yl-isoxazole-3-carboxylic acid(2-imidazol-1-yl-ethyl)-amide,
   5-thiophen-2-yl-isoxazole-3-carboxylic acid(2-pyrazol-1-yl-ethyl)-amide,
   5-thiophen-2-yl-isoxazole-3-carboxylic acid(2-[1,2,4]triazol-1-yl-ethyl)-amide,
   5-thiophen-2-yl-isoxazole-3-carboxylic acid(2-[1,2,3]triazol-2-yl-ethyl)-amide,
   5-thiophen-2-yl-isoxazole-3-carboxylic acid(2-[1,2,3]triazol-1-yl-ethyl)-amide,
   5-thiophen-2-yl-isoxazole-3-carboxylic acid(2-pyridin-3-yl-ethyl)-amide,
   5-thiophen-2-yl-isoxazole-3-carboxylic acid(2-pyridin-4-yl-ethyl)-amide,
   5-(5-bromo-thiophen-2-yl)-isoxazole-3-carboxylic acid (3-imidazol-1-yl-propyl)-amide,
   5-thiophen-3-yl-isoxazole-3-carboxylic acid(3-[1,2,4]-triazol-1-yl-propyl)-amide,
   5-thiophen-3-yl-isoxazole-3-carboxylic acid(3-imidazol-1-yl-propyl)-amide,
   5-thiophen-3-yl-isoxazole-3-carboxylic acid(2-imidazol-1-yl-ethyl)-amide,
   5-thiophen-3-yl-isoxazole-3-carboxylic acid(2-[1,2,4]-triazol-1-yl-ethyl)-amide,
   5-thiophen-2-yl-isoxazole-3-carboxylic acid[2-(pyridin-2-yl-oxy)-ethyl]-amide,
   5-thiophen-2-yl-isoxazole-3-carboxylic acid[2-(1-methyl-1H-tetrazol-5-yl-sulfanyl)-ethyl]-amide, and
   5-thiophen-2-yl-isoxazole-3-carboxylic acid[3-(4H-[1,2,4]triazol-3-yl-sulfanyl)-propyl]-amide.

18. The method of claim 2, wherein the compound is selected from:
   5-furan-2-yl-isoxazole-3-carboxylic acid(2-imidazol-1-yl-ethyl)-amide,
   5-furan-2-yl-isoxazole-3-carboxylic acid(2-pyridin-4-yl-ethyl)-amide,
   5-furan-2-yl-isoxazole-3-carboxylic acid(2-[1,2,4]triazol-1-yl-ethyl)-amide,
   5-thiophen-2-yl-isoxazole-3-carboxylic acid(3-[1,2,4]-triazol-1-yl-propyl)-amide,
   5-thiophen-3-yl-isoxazole-3-carboxylic acid(3-[1,2,4]-triazol-1-yl-propyl)-amide,
   5-thiophen-3-yl-isoxazole-3-carboxylic acid(3-imidazol-1-yl-propyl)-amide,
   5-thiophen-2-yl-isoxazole-3-carboxylic acid[2-(1-methyl-1H-tetrazol-5-yl-sulfanyl)-ethyl]-amide,
   5-thiophen-2-yl-isoxazole-3-carboxylic acid[3-(4H-[1,2,4]triazol-3-yl-sulfanyl)-propyl]-amide, and
   5-furan-2-yl-isoxazole-3-carboxylic acid[2-(4-methyl-4H-[1,2,4]triazol-3-sulfonyl)-ethyl]-amide.

19. The method of claim 2, wherein the compound is 5-furan-2-yl-isoxazole-3-carboxylic acid (2-pyridin-4-yl-ethyl)-amide.

* * * * *

UNITED STATES PATENT AND TRADEMARK OFFICE
CERTIFICATE OF CORRECTION

| | | |
|---|---|---|
| PATENT NO. | : 8,518,978 B2 | Page 1 of 1 |
| APPLICATION NO. | : 12/666785 | |
| DATED | : August 27, 2013 | |
| INVENTOR(S) | : Hwang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this
Thirtieth Day of December, 2014

Michelle K. Lee
*Deputy Director of the United States Patent and Trademark Office*